United States Patent
De Nys et al.

(10) Patent No.: US 12,295,980 B2
(45) Date of Patent: May 13, 2025

(54) **METHOD FOR PRODUCING AN *Asparagopsis* OIL COMPOSITION**

(71) Applicant: FutureFeed Pty Limited, Brisbane (AU)

(72) Inventors: Rocky De Nys, Mysterton (AU); Marie Elisabeth Magnusson, Tauranga (NZ)

(73) Assignee: FutureFeed Pty Limited, Brisbane (AU)

( * ) Notice: Subject to any disclaimer, the term of this patent is extended or adjusted under 35 U.S.C. 154(b) by 884 days.

(21) Appl. No.: 17/299,968

(22) PCT Filed: Dec. 6, 2019

(86) PCT No.: PCT/AU2019/051335
§ 371 (c)(1),
(2) Date: Jun. 4, 2021

(87) PCT Pub. No.: WO2020/113279
PCT Pub. Date: Jun. 11, 2020

(65) Prior Publication Data
US 2022/0031780 A1    Feb. 3, 2022

(30) Foreign Application Priority Data
Dec. 6, 2018    (AU) ................ 2018904642

(51) Int. Cl.
| | | |
|---|---|---|
| *A61K 36/04* | (2006.01) | |
| *A23K 20/158* | (2016.01) | |
| *A23K 50/10* | (2016.01) | |
| *A61K 31/02* | (2006.01) | |
| *A61K 31/19* | (2006.01) | |

(52) U.S. Cl.
CPC ............ *A61K 36/04* (2013.01); *A23K 20/158* (2016.05); *A23K 50/10* (2016.05); *A61K 31/02* (2013.01); *A61K 31/19* (2013.01); *A61K 2236/35* (2013.01)

(58) Field of Classification Search
CPC .................................................. A61K 36/04
See application file for complete search history.

(56) References Cited

FOREIGN PATENT DOCUMENTS

| | | |
|---|---|---|
| WO | 2015/006541 A2 | 1/2015 |
| WO | 2015/109362 A2 | 7/2015 |

OTHER PUBLICATIONS

Burreson et al., "Volatile halogen compounds in the alga *Asparagopsis taxiformis* (Rhodophyta)", J. Agri. Food Chem., vol. 24, No. 4, 1976, p. 856-861. (Year: 1976).*
International Search Report and Written Opinion of the International Searching Authority for International Patent Application No. PCT/AU2019/051335 mailed Feb. 4, 2020, 10 pages.
Li, X. et al., "*Asparagopsis taxiformis* decreases enteric methane production from sheet", Animal Production Science, 1-9 (2018).
Machado, L. et al., "Effects of Marine and Freshwater Macroalgae on In Vitro Total Gas and Methane Production", PLOS One, 9(1): 1-11 (Jan. 2014).
Machado, L. et al., "Dose-response effects of Asparagopsis taxiformis and *Oedogonium* sp. on in vitro fermentation and methane production", Journal of Applied Phycology, 28: 1443-1452 (2016).
Machado, L. et al., "Identification of bioactives from the red seaweek Asparagopsis taxiformis that promote antimethanogenic activity in vitro", Journal of Applied Phycology, 28: 3117-3126 (2016).
Machado, L. et al., "In Vitro Response of Rumen Microbiota to the Antimethanogenic Red Macroalga *Asparagopsis taxiformis*", Microbial Ecology, 75: 811-818 (2018).
Vucko, M. et al., "The effects of processing on the in vitro antimethanogenic capacity and concentration of secondary metabolites of Asparagopsis taxiformis", Journal of Applied Phycology, 29: 1577-1586 (2017).
Hino, T. et al., "Maintenance of Protozoa and Methanogens, and Fiber Digestion in Rumen-Simulating Continuous Culture", J. Gen. Appl. Microbiol., 39: 35-45 (1993).
Li, X., "Eremophila glabra reduces methane production in sheep", Thesis, The University of Western Australia, School of Animal Biology, 1-111 (2013).
Paul, N. et al., "Chemical defence against bacteria in the red alga *Asparagopsis armata*: linking structure with function", Marine Ecology Progress Series, 306: 87-101 (2006).

* cited by examiner

*Primary Examiner* — Gina C Justice
(74) *Attorney, Agent, or Firm* — Merchant & Gould P.C.

(57) ABSTRACT

The field of the invention relates to processes for preparing *Asparagopsis* oil compositions, comprising extracting at least one bioactive from a biomass of *Asparagopsis* into an oil to form the compositions. These compositions are suitable for reducing total gas production and/or methane production in a ruminant or pseudo-ruminant animal.

14 Claims, 10 Drawing Sheets

METHOD FOR PRODUCING AN *Asparagopsis* OIL COMPOSITION

This application is a National Stage Application of PCT/AU2019/051335, filed 6 Dec. 2019, which claims benefit of Serial No. 2018904642, filed 6 Dec. 2018 in Australian, and which applications are incorporated herein by reference. To the extent appropriate, a claim of priority is made to each of the above disclosed applications.

FIELD OF THE INVENTION

The field of the invention relates to processes for preparing compositions suitable for reducing total gas production and/or methane production in a ruminant animal.

BACKGROUND OF THE INVENTION

Methane ($CH_4$) is a greenhouse gas (GHG) produced primarily by methanogenic microbes that are found in natural ecosystems (e.g. wetlands, oceans and lakes) and the gastrointestinal tract of invertebrates and vertebrates, such as termites and ruminants. Every year ~429-507 Tg of $CH_4$ are removed from the atmosphere and ~40 Tg from the stratosphere through reactions with hydroxyl (OH) radicals; and ~30 Tg by $CH_4$-oxidizing bacteria in soil.

Nevertheless, anthropogenic GHG emissions have been increasing rapidly, with the $CH_4$ concentration in the atmosphere now more than twofold higher than in the early 1800s. Methane is very effective at absorbing solar infrared radiation and has a global warming potential 25 times greater than $CO_2$. Consequently, its accumulation in the atmosphere contributes considerably to climate change. One of the main sources of anthropogenic $CH_4$ can be attributed to agricultural activities, including ruminant livestock.

According to a recent UN report, cattle-rearing generates more global warming greenhouse gases, as measured in $CO_2$ equivalents, than transportation. In Australia, ruminants are estimated to contribute ~10% of the total GHG emissions. Ruminants produce $CH_4$ as a by-product of the anaerobic microbial fermentation of feeds in the rumen and, to a lesser extent, in the large intestine. The ruminal microbial community is highly diverse and composed of bacteria, protozoa, fungi, and bacteriophages that act collectively to ferment ingested organic matter (OM), resulting in $CO_2$, $H_2$, volatile fatty acids (VFAs), and formates. Methanogenic archaea present in the rumen use these end-products and produce $CH_4$. Although the production of $CH_4$ reduces the partial pressure of $H_2$, which could otherwise inhibit rumen fermentation, it also reduces the amount of energy and carbon available for formation of VFAs essential for ruminant nutrition. Most of the $CH_4$ produced in ruminants is exhaled and belched by the animal and represents a loss of up to 12% of gross energy intake.

Mitigation strategies that reduce enteric $CH_4$ formation are important, and methods of reducing total gas production and/or methane production in ruminant animals represent a major challenge.

SUMMARY OF THE INVENTION

In one aspect, the present invention provides a process for preparing an *Asparagopsis* oil composition, said process comprising the steps of: providing a biomass of *Asparagopsis*; providing at least one oil; and contacting the biomass with the at least one oil under conditions to extract at least one bioactive agent from the biomass into the at least one oil to form the *Asparagopsis* oil composition.

In one embodiment of the process, the step of contacting the biomass with the at least one oil may include homogenising the biomass in the at least one oil. In another embodiment of the process, the biomass may be separated from the at least one oil after the step of contacting the biomass with the at least one oil.

In another aspect of the process, the ratio of biomass (in grams) to the at least one oil (in millilitres) may be greater than 0.3:1. In one embodiment, the ratio of biomass (in grams) to the at least one oil (in millilitres) is greater than 0.6:1.

In another embodiment, the ratio of biomass (in grams) to the at least one oil (in millilitres) is greater than 0.9:1. In another embodiment, the ratio of biomass (in grams) to the at least one oil (in millilitres) is greater than 1.2:1.

In another aspect of the process, the conditions to extract at least one bioactive agent from the biomass into the at least one oil may be performed for a period of at least 1 day. In one embodiment, the extraction is performed for 2 days. In another embodiment, the extraction is performed for 3 days. In another embodiment, the extraction is performed for 4 days. In another embodiment, the extraction is performed for 5 days. In another embodiment, the extraction is performed for 6 days. In another embodiment, the extraction is performed for 7 days. In another embodiment, the extraction is performed for 8 days. In another embodiment, the extraction is performed for 9 days. In another embodiment, the extraction is performed for 10 days. In yet another embodiment, the extraction is performed for 11 days.

In another aspect of the process, the conditions to extract at least one bioactive agent from the biomass into the at least one oil may be performed at a temperature of about 4° C.

In one embodiment of the process, prior to the step of separating the biomass from the at least one oil, the biomass in contact with the at least one oil may be heated. In this embodiment, the heating is performed such that a gel which may comprise the at least one bioactive agent releases the at least one bioactive agent to the at least one oil. In one embodiment, the heating may be performed at a temperature of 60° C. In the above embodiments, the heating may be performed for a period of one hour.

In one aspect of the present invention, the biomass of *Asparagopsis* may be *Asparagopsis taxiformis*. In another aspect, the biomass of *Asparagopsis* may be *Asparagopsis armata*. In another aspect, the biomass of *Asparagopsis* may be *Asparagopsis taxiformis* and *Asparagopsis armata*.

In one embodiment of the process, the step of providing a biomass of *Asparagopsis* does not include air drying of the biomass. In another embodiment, the step of providing a biomass of *Asparagopsis* comprises collecting the biomass into the at least one oil.

In another aspect, the at least one oil comprises an edible oil. In one embodiment, the edible oil may be selected from the group consisting of almond oil, apricot oil, argan oil, avocado oil, brazil nut oil, canola oil, cashew oil, coconut oil, colza oil, corn oil, copra oil, cottonseed oil, diacylglycerol oil, flaxseed oil, grapefruit seed oil, grapeseed oil, hazelnut oil, hemp oil, lemon oil, linseed oil, macadamia oil, mustard oil, olive oil, orange oil, palm oil, palm kernel oil, peanut oil, pecan oil, pine nut oil, pistachio oil, pumpkin seed oil, rapeseed oil, rice bran oil, safflower oil, sesame oil, soybean oil, sunflower oil, walnut oil, and vegetable oil or any combination thereof.

In another aspect, the at least one bioactive agent may be an anti-methanogenic agent. In one embodiment, the at least one bioactive agent may be selected from the group consisting of bromochloroacetic acid (BCA), bromoform (BF), dibromoacetic acid (DBA), and dibromochloromethane (DBCM). In another embodiment, the anti-methanogenic agent is BF. In another embodiment, the anti-methanogenic agent is DBCM. In another embodiment, the anti-methanogenic agents are BF and DBCM.

In another aspect, a level of the at least one bioactive agent extracted from the biomass into the at least one oil is increased relative to the level of the at least one bioactive agent extracted from an equivalent amount of biomass into water. In one embodiment, the at least one bioactive agent is an anti-methanogenic agent, wherein a level of the anti-methanogenic agent extracted from the biomass into the at least one oil is not reduced by more than 20% following storage for 65 weeks at 25° C., wherein the at least one anti-methanogenic agent is BF and/or DBCM.

In one embodiment, a level of the at least one bioactive agent extracted from the biomass into the at least one oil is not significantly reduced following storage for 12 weeks at 25° C. In another embodiment, the level of the at least one bioactive agent extracted from the biomass into the at least one oil is not significantly reduced following storage for 65 weeks at 4° C.

In another aspect, the *Asparagopsis* oil composition formed by the process comprises at least 0.1 milligrams of bromoform per millilitre of extract. In one embodiment, the *Asparagopsis* oil composition formed by the process comprises at least 1 milligram of bromoform per millilitre of extract. In another embodiment, the *Asparagopsis* oil composition formed by the process comprises at least 2 milligrams of bromoform per millilitre of extract. In another embodiment, the *Asparagopsis* oil composition formed by the process comprises at least 3 milligrams of bromoform per millilitre of extract. In another embodiment, the *Asparagopsis* oil composition formed by the process comprises at least 4 milligrams of bromoform per millilitre of extract.

In another aspect, the present invention provides an *Asparagopsis* oil composition comprising at least one oil and at least one anti-methanogenic agent. In one embodiment, the *Asparagopsis* may be *Asparagopsis taxiformis*. In another embodiment, the *Asparagopsis* may be *Asparagopsis armata*. In another embodiment, the *Asparagopsis* may be *Asparagopsis taxiformis* and *Asparagopsis armata*.

In the above embodiments, the at least one oil may comprise an edible oil. In this embodiment, the edible oil may be selected from the group consisting of almond oil, apricot oil, argan oil, avocado oil, brazil nut oil, canola oil, cashew oil, coconut oil, colza oil, corn oil, copra oil, cottonseed oil, diacylglycerol oil, flaxseed oil, grapefruit seed oil, grapeseed oil, hazelnut oil, hemp oil, lemon oil, linseed oil, macadamia oil, mustard oil, olive oil, orange oil, palm oil, palm kernel oil, peanut oil, pecan oil, pine nut oil, pistachio oil, pumpkin seed oil, rapeseed oil, rice bran oil, safflower oil, sesame oil, soybean oil, sunflower oil, walnut oil, and vegetable oil, or any combination thereof.

In another aspect of the *Asparagopsis* oil composition, the at least one anti-methanogenic agent may be selected from the group consisting of bromochloroacetic acid (BCA), bromoform (BF), dibromoacetic acid (DBA), and dibromochloromethane (DBCM).

In one embodiment of the *Asparagopsis* oil composition, a level of the at least one anti-methanogenic agent is not significantly reduced following storage for 12 weeks at 25° C. In another embodiment, the level of the at least one anti-methanogenic agent is not significantly reduced following storage for 65 weeks at 4° C. In another embodiment, the level of the at least one anti-methanogenic agent is not reduced by more than 20% following storage for 65 weeks at 25° C. In the above embodiments, the at least one anti-methanogenic agent may be BF and/or DBCM. In another embodiment, the level of the at least one anti-methanogenic agent is not reduced by more than 50% following storage for 65 weeks at 4° C. or 25° C. In this embodiment, the at least one anti-methanogenic agent may be DBA.

In one embodiment, the *Asparagopsis* oil composition may have a concentration of the at least one anti-methanogenic agent of at least 0.1 milligrams per millilitre of extract. In another embodiment, the *Asparagopsis* oil composition may have a concentration of the at least one anti-methanogenic agent of at least 1 milligram per millilitre of extract. In another embodiment, the *Asparagopsis* oil composition may have a concentration of the at least one anti-methanogenic agent of at least 2 milligrams per millilitre of extract. In another embodiment, the *Asparagopsis* oil composition may have a concentration of the at least one anti-methanogenic agent of at least 3 milligrams per millilitre of extract. In another embodiment, the *Asparagopsis* oil composition may have a concentration of the at least one anti-methanogenic agent of at least 4 milligrams per millilitre of extract.

In another aspect, the present invention provides a feed supplement for reducing total gas production and/or methane production in a ruminant animal, said supplement comprising an effective amount of an *Asparagopsis* oil composition as described herein.

In another aspect, the present invention provides a feed for a ruminant animal, wherein said feed is supplemented with a feed supplement as described herein.

In another aspect, the present invention provides a method for reducing total gas production and/or methane production in a ruminant animal comprising administering to said ruminant animal an effective amount of an *Asparagopsis* oil composition as described herein. In one embodiment, the method may comprise maintenance of an effective level of a desirable volatile fatty acid. In this embodiment, the desirable volatile fatty acid may comprise acetate and propionate, and wherein maintenance comprises a decrease in a ratio of acetate to propionate. In another embodiment, the method may comprise maintenance of a level of degraded organic matter and/or dry matter.

In another aspect of the method, the *Asparagopsis* oil composition may be administered at a dose equivalent to at least 3% of organic matter administered to the ruminant animal. In one embodiment, the *Asparagopsis* oil composition may be administered at a dose equivalent to at least 2% of organic matter administered to the ruminant animal. In another embodiment, the *Asparagopsis* oil composition may be administered at a dose equivalent to at least 1% of organic matter administered to the ruminant animal. In another embodiment, the *Asparagopsis* oil composition may be administered at a dose equivalent to at least 0.5% of organic matter administered to the ruminant animal. In another embodiment, the *Asparagopsis* oil composition may be administered at a dose equivalent to at least 0.25% of organic matter administered to the ruminant animal. In another embodiment, the *Asparagopsis* oil composition may be administered at a dose equivalent to at least 0.125% of organic matter administered to the ruminant animal. In another embodiment, the *Asparagopsis* oil composition may be administered at a dose equivalent to at least 0.067% of organic matter administered to the ruminant animal.

In another aspect of the above method, the ruminant animal may be selected from the members of the Ruminantia and Tylopoda suborders. In one embodiment of this aspect, the ruminant animal may be cattle or sheep. In another embodiment, the ruminant animal is cattle.

DETAILED DESCRIPTION

The present invention relates to methods for preparing bioactive *Asparagopsis* oil compositions, including *Asparagopsis* oil compositions suitable for reducing total gas production (TGP) and/or methane ($CH_4$) production by a ruminant animal. In particular, the present inventors have shown *Asparagopsis* oil compositions comprising halogenated secondary metabolites with bioactive properties can be prepared, and importantly, the present inventors have also shown that the levels of halogenated secondary metabolites in the *Asparagopsis* oil compositions are stable over long periods of time.

Figure 1:
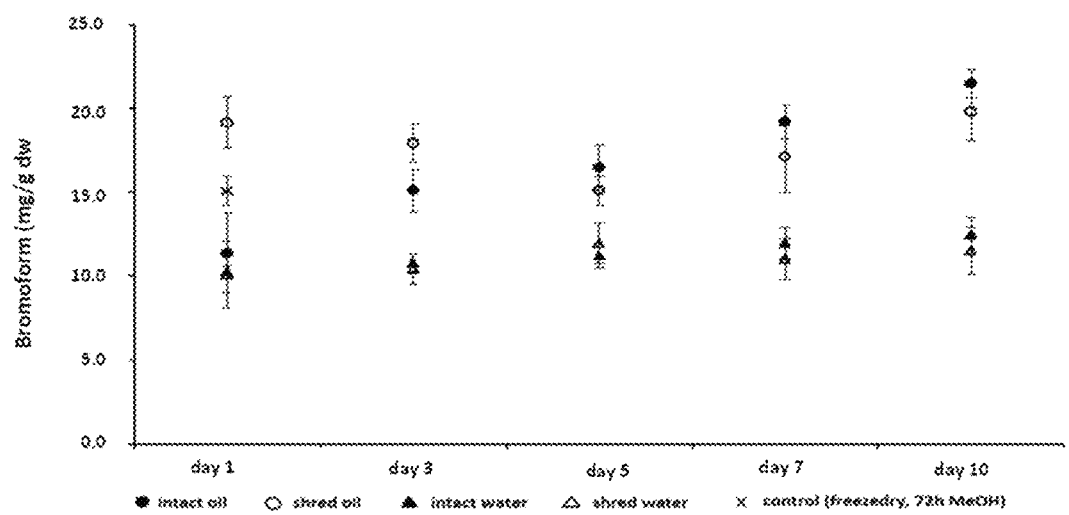
FIG. 1 shows amount of a bioactive, bromoform (an anti-methanogenic agent) in compositions prepared by extracting a biomass of *Asparagopsis* into oil or water, including compositions prepared by homogenising the biomass of *A. taxiformis* in oil or water ("shred"), or non-homogenised biomass in oil or water ("intact"), for 1, 3, 5, 7 and 10 days. Black diamond represents the standard method of extraction using freeze-dried biomass, steeped in methanol for 72 h. Data are presented as mean+se, n=3.
Figure 3:
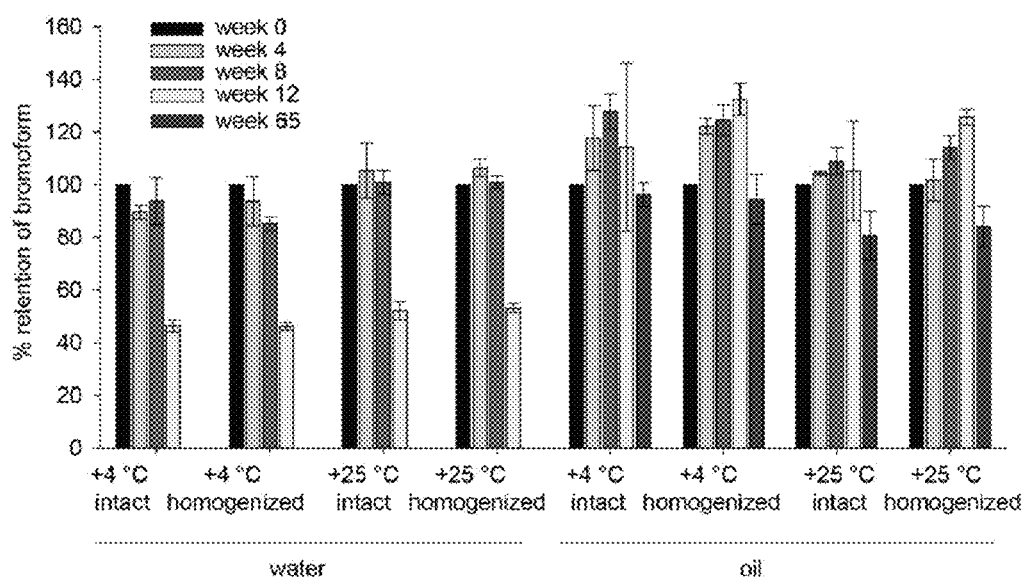
FIG. 3 shows the retention of a bioactive, bromoform (an anti-methanogenic agent) in compositions prepared by extracting a biomass of *Asparagopsis* into oil or water, including compositions prepared by homogenising the biomass of *A. taxiformis* in oil or water ("shred"), or non-homogenised biomass in oil or water ("intact")), at t=0 and after 4, 8, 12, and 65 weeks of storage (at either 4° C. or 25° C.). Data are presented as mean+se, n=3.

FIG. 1 shows that *Asparagopsis* oil compositions comprising a bioactive molecule can be prepared by contacting a biomass of *Asparagopsis* with an oil, and that the levels of bioactive are increased by homogenising the biomass in the oil. FIG. 3 shows that *Asparagopsis* oil compositions prepared by contacting a biomass of *Asparagopsis* with an oil, with or without homogenisation, retain high levels of a bioactive for extended periods of time, when stored at either room temperature (25° C.) or at 4° C.

The invention therefore relates to a process for preparing an *Asparagopsis* oil composition, said process comprising the steps of:
(a) providing a biomass of *Asparagopsis*;
(b) providing at least one oil; and
(c) contacting the biomass with the at least one oil under conditions to extract at least one anti-methanogenic agent from the biomass into the at least one oil.

*Asparagopsis* has a heteromorphic life history with two free-living life history stages—a gametophyte (large foliose form) and a sporophyte (or tetrasporophyte—smaller, filamentous form). Historically, the tetrasporophyte was recognised as a separate genus (Falkenbergia). Therefore, the term "*Asparagopsis*" as used herein refers to the genus *Asparagopsis*, and other taxonomic classifications now known to belong to the genus *Asparagopsis*.

There are at least two recognised species of *Asparagopsis*, one tropical/sub-tropical (*Asparagopsis taxiformis*) and one temperate (*Asparagopsis armata*) which are present throughout the world.

In one embodiment, the species of *Asparagopsis* is selected from.

*Asparagopsis taxiformis* or *Asparagopsis armata*.

In another aspect, a biomass of at least one species of red marine macroalgae selected from a species of belonging to the other genera of red seaweed in the family Bonnemaisoniaceae to which *Asparagopsis* belongs (for example, Bonnemaisonia, Delisea, Ptilonia, Leptophyllis and Pleuroblepharidella) is used in place of a biomass of *Asparagopsis* in the methods and compositions provided herein. Without wishing to be bound by theory, the six genera of red seaweed in the family Bonnemaisoniaceae (for example *Asparagopsis*, Bonnemaisonia, Delisea, Ptilonia, Leptophyllis and Pleuroblepharidella), produce and store bioactive halogenated secondary metabolites with bioactive properties, including the anti-methanogenic compounds described herein.

As used herein the term "providing a biomass" includes the provision or use of a biomass of *Asparagopsis* removed from water immediately prior to contacting the biomass with the at least one oil. In one embodiment the biomass of *Asparagopsis* is collected from its environment and placed directly into the at least one oil. In another embodiment the biomass of *Asparagopsis* is contacted with the at least one oil within 5, 4, 3, 2, or 1 hours from the removal of biomass from its environment.

In one embodiment, water is removed from the biomass by blotting dry the biomass prior to contacting the biomass with the at least one oil.

In one embodiment the biomass of *Asparagopsis* is not a freeze dried biomass of *Asparagopsis*.

In another embodiment the biomass of *Asparagopsis* is not an air dried biomass of *Asparagopsis*.

As used herein the term "at least one oil" includes a single type of oil, or compositions comprising a single type of oil, or a mixture of two or more oils, or a composition comprising a mixture of two or more oils. The at least one oil includes an oil suitable for application to, administration to, or feeding to, an animal.

In one embodiment, the at least one oil comprises an edible oil.

In one embodiment, the edible oil is selected from the group consisting of almond oil, apricot oil, argan oil, avocado oil, brazil nut oil, canola oil, cashew oil, coconut oil, colza oil, corn oil, copra oil, cottonseed oil, diacylglycerol oil, flaxseed oil, grapefruit seed oil, grapeseed oil, hazelnut oil, hemp oil, lemon oil, linseed oil, macadamia oil, mustard oil, olive oil, orange oil, palm oil, palm kernel oil, peanut oil, pecan oil, pine nut oil, pistachio oil, pumpkin seed oil, rapeseed oil, rice bran oil, safflower oil, sesame oil, soybean oil, sunflower oil, walnut oil, and vegetable oil or any combination thereof.

As used herein, the term "oil" means any non-polar, hydrophobic substance which is typically a liquid at ambient temperature and pressure. Oils may be derived from animals, vegetables, or petrochemicals, and typically have a high carbon and hydrogen content. The oil is preferably an edible oil, and preferably digestible by a ruminant animal. Typically, an oil of vegetable origin is extracted from the seeds or fruits of plants, and is typically comprised primarily of triglycerides. The term "vegetable oil" is a generic term to indicate that the oil is of primarily or exclusively vegetable origin, and may comprise a mixture of one or more oils of vegetable origin or from differing origins.

The present inventors have demonstrated that bioactive agents are rapidly extracted from a biomass of *Asparagopsis* into oil. For example, FIG. 1 demonstrates that within 24 hours, the levels of bromoform extracted from a biomass/oil mixture that has been homogenised are greater than the levels of bromoform extracted from the freeze dried biomass using methanol. FIG. 1 also demonstrates that within 72 hours, the level of bromoform extracted from a biomass/oil mixture that has not been homogenised is the same as the level of bromoform extracted from freeze dried biomass. FIG. 1 also demonstrates that within 120 hours, the levels of bromoform extracted from a biomass/oil mixture that has not been homogenised are greater than the levels of bromoform extracted from freeze dried biomass using methanol.

As used herein the term "contacting" includes mixing the biomass with the at least one oil to form a biomass/oil mixture, and retaining the biomass oil mixture for a period of time and at a temperature suitable to extract at least one bioactive agent from the biomass into the oil of the biomass/oil mixture.

The term contacting includes retaining the biomass oil mixture at different suitable temperatures.

The temperature at which the biomass can be contacted with the at least one oil is not limited, insofar as the anti-methanogenic agent does not evaporate/sublime appreciably from the oil, and/or does not degrade appreciably at the temperature at which the contacting takes place. The temperature may be selected from the group consisting of $-78°$ C. to $-50°$ C., $-50°$ C. to $-20°$ C., $-20°$ C. to $-5°$ C., $-5°$ C. to $0°$ C., $-5°$ C. to $4°$ C., $0°$ C. to $4°$ C., $4°$ C. to $10°$ C., $10°$ C. to $20°$ C., $20°$ C. to $25°$ C., $25°$ C. to $30°$ C., $30°$ C. to $40°$ C., $40°$ C. to $50°$ C., $50°$ C. to $60°$ C., $60°$ C. to $70°$ C., $70°$ C. to $80°$ C., $80°$ C. to $90°$ C., and $90°$ C. to $100°$ C. In some embodiments, the temperature may be selected from the group consisting of $-78°$ C., $-20°$ C., $-5°$ C., $0°$ C., $1°$ C., $2°$ C., $3°$ C., $4°$ C., $5°$ C., $6°$ C., $7°$ C., $8°$ C., $9°$ C., $10°$ C., $20°$ C., $21°$ C., $22°$ C., $23°$ C., $24°$ C., $25°$ C., $26°$ C., $27°$ C., $28°$ C., $29°$ C. and $30°$ C. In one embodiment, the temperature is preferably about $4°$ C. In another embodiment, the temperature is preferably about $25°$ C. Suitable temperatures can be achieved using freezers, fridges, air-conditioners and the like.

As used herein, the term "room temperature" is used to indicate normal ambient temperature. As one of skill in the art will appreciate, ambient conditions will differ depending on the geographical location and time of year, such that room temperatures may vary from below zero Celsius to above $40°$ C. Typically, room temperature is considered to be between about $20°$ C. and about $25°$ C., and for the purposes of the experiments carried out in Townsville, Queensland, room temperature has been taken to mean about $25°$ C.

The present inventors have demonstrated that if a large amount of biomass of *Asparagopsis* is contacted with a relatively small volume of oil, the formation of a gel occurs which hinders extraction of the one or more bioactive agents into the oil. To increase the yield of the extracted bioactive (e.g. anti-methanogenic) agent, the gel and/or biomass and/or oil can be heated to release more of the at least one bioactive (e.g. anti-methanogenic) agent to the at least one oil. For example, FIGS. 8 and 9 demonstrate that heating a sample of biomass contacted with the at least one oil, at $60°$ C. for 1 hour, resulted in up to 20% more bioactive (e.g. anti-methanogenic) agent extracted into the oil compared to non-heating of the samples (see data for "120 g+heat" vs "120 g" in FIGS. 8 and 9).

The temperature at which the biomass contacted with the at least one oil can be heated to, to release at least one bioactive (e.g. anti-methanogenic) agent to the at least one oil, is not limited, insofar as that the at least one bioactive (e.g. anti-methanogenic) agent does not evaporate/sublime appreciably from the oil, and/or does not degrade appreciably at the temperature at which the heating takes place. The temperature may be selected from the group consisting of $25°$ C. to $30°$ C., $30°$ C. to $40°$ C., $40°$ C. to $50°$ C., $50°$ C. to $60°$ C., $60°$ C. to $70°$ C., $70°$ C. to $80°$ C., $80°$ C. to $90°$ C., and $90°$ C. to $100°$ C. In some embodiments, the temperature may be selected from the group consisting of 30° C., 40° C., 50° C., 60° C., 70° C. and 80° C. In one embodiment, the temperature is preferably about 60° C.

The time for which the biomass contacted with the at least one oil can be heated to, to release at least one bioactive (e.g. anti-methanogenic) agent to the at least one oil, is not limited, insofar as the at least one bioactive (e.g. anti-methanogenic) agent does not evaporate/sublime appreciably from the oil, and/or does not degrade appreciably during heating. The time period may be selected from the group consisting of 1 second to 1 minute, 1 minute to 2 minutes, 2 minutes to 5 minutes, 5 minutes to 10 minutes, 10 minutes to 20 minutes, 20 minutes to 30 minutes, 30 minutes to 40 minutes, 40 minutes to 50 minutes, 50 minutes to 60 minutes, 60 minutes to 70 minutes, 70 minutes to 80 minutes, 80 minutes to 90 minutes, 1.5 hours to 2 hours, 2 hours to 3 hours, 3 hours to 4 hours, and 4 hours to 5 hours. In some embodiments, the time period may be selected from the group consisting of 1 minute, 5 minutes, 10 minutes, 20 minutes, 30 minutes, 40 minutes, 50 minutes, 1 hour, 2 hours, and 3 hours. In one embodiment, the time period that the biomass contacted with the at least one oil is heated for, is preferably about 1 hour.

When the biomass/oil mixture is not being heated to release at least one bioactive (e.g. anti-methanogenic) agent to the at least one oil, the amount of time that the biomass can be in contact with the at least one oil, under conditions to extract at least one bioactive (e.g. anti-methanogenic) agent from the biomass into the at least one oil, is not particularly limited. As one of skill in the art will appreciate, it is desired that the concentration of the at least one bioactive (e.g. anti-methanogenic) agent in the oil will reach or nearly reach an equilibrium level, such that the amount of the at least one bioactive (e.g. anti-methanogenic) agent in the at least one oil is maximised. Thus, the contacting of biomass with the at least one oil under conditions to the extract at least one bioactive (e.g. anti-methanogenic) agent from the biomass into the at least one oil, can be performed for a period selected from the group consisting of: 1 minute to 1 hour, 1 hour to 2 hours, 2 hours to 3 hours, 3 hours to 4 hours, 4 hours to 5 hours, 5 hours to 6 hours, 6 hours to 12 hours, 12 hours to 24 hours, 1 day to 2 days, 2 days to 3 days, 3 days to 4 days, 4 days to 5 days, 5 days to 6 days, 6 days to 7 days, 7 days to 8 days, 8 days to 9 days, 9 days to 10 days, 10 days to 14 days, 2 weeks to 3 weeks, and 3 weeks to 1 month. In some embodiments, the contacting can be performed for a period selected from the group consisting of 1 minute, 2 minutes, 5 minutes, 10 minutes, 20 minutes, 30 minutes, 1 hour, 2 hours, 5 hours, 10 hours, 1 day, 2 days, 3 days, 4 days, 5 days, 6 days, 7 days, 8 days, 9 days, 10 days, and 2 weeks. In some embodiments, the contacting can be performed for a period at least 1, 2, 3, 4, 5, 4, 6, 7, 8, 9, or 10 days.

The step of contacting the biomass with the at least one oil may also include homogenising the biomass in the at least one oil. As used herein, the term "homogenising" means to break up the biomass to facilitate release of at least one anti-methanogenic agent from the biomass, which can then be extracted into the at least one oil. The homogenising can take place by any means known in the art, such as crushing, grinding, milling, blending, cutting, slicing, or dicing.

In one embodiment, homogenising may be performed to obtain a homogenous mixture such that even distribution of the biomass, bioactive agent and/or oil in the composition, to a feed source for an animal, is facilitated.

In one embodiment the bioactive agent is an agent that has a biological effect on an animal, preferably a ruminant animal. The biological effect may be any effect on the behaviour or physiology of the animal, or it may even affect microorganisms within said animal. For example, the biological effect may be inhibition of methanogenesis. The bioactive agent responsible for inhibition of methanogenesis is not particularly limited, and is intended to include all agents that inhibit methanogenesis, including but not limited to secondary metabolites. *Asparagopsis* produces secondary metabolites including halogenated low molecular weight compounds, in particular brominated and chlorinated haloforms. Many of these compounds have strong antimicrobial properties and inhibit a wide range of microorganisms, including Gram-positive and Gram-negative bacteria, as well as *mycobacterium* and fungus activities, and therefore may be involved in contributing to the effects described herein. Secondary metabolites from *Asparagopsis* also inhibit protozoans.

In one embodiment the bioactive agent is an agent that reduces total gas production (TGP), and/or an agent that reduces methane, produced by a ruminant animal.

As used herein, the term "reducing" includes the reduction of amount of substance in comparison with a reference. For example, the reduction in the amount of total gas and/or methane produced by a ruminant animal or animals administered an *Asparagopsis* oil composition as described herein, relative to an animal or animals not administered a composition comprising an *Asparagopsis* oil composition as described herein. The reduction can be measured in vitro with an artificial rumen system that simulates anaerobic fermentation, or in vivo with animals confined in respiration chambers. It is within the knowledge and skill of those trained in the art to assess enteric methanogenesis by a ruminant animal.

As used herein, the term 'reducing total gas production' refers to the reduction of the total amount of gas produced, for example the amount of total gas produced in the gastro-intestinal tract. The term includes the collective volume of all gasses generated as a result of anaerobic fermentation, for example, in the systems described herein. Fermentation in the rumen and the gut of a ruminant gives rise to production of gas, including methane. The present invention aims to reduce this process, such as to reduce the total amount of gas produced in the gastro-intestinal tract. It is within the knowledge and skill of those trained in the art to assess total gas production by a ruminant animal.

As used herein, the term 'reducing methane production' refers to the reduction of methane produced in the gastro-intestinal tract. The term includes the specific volume of methane generated as a result of anaerobic fermentation, for example, in the systems described herein. Fermentation in the rumen and the gut of a ruminant gives rise to production of methane. The present invention aims to reduce this process, such as to reduce the total amount of methane produced in the gastro-intestinal tract. It is within the knowledge and skill of those trained in the art to assess methane production by a ruminant animal.

As used herein the term "anaerobic fermentation" is intended to include anaerobic fermentation in vivo, for example, in a ruminant animal.

As used herein, the term "anti-methanogenic agent" means any bioactive compound that inhibits methanogenesis in a ruminant animal. Such compounds are typically halogenated secondary metabolites including at least the following: bromochloroacetic acid, bromochloromethane, 2-bromoethanesulfonic acid, chloral hydrate, chloroform, iodopropane, bromoform (BF), dibromoacetic acid (DBA), and dibromochloromethane (DBCM).

For example, the present inventors have demonstrated in FIGS. 4, 5, 6 and 7 that *Asparagopsis* oil compositions comprising dibromochloromethane (DBCM) and/or dibromoacetic acid (DBA) can be prepared by contacting a biomass of *Asparagopsis* with an oil, with homogenisation. High levels of the bioactive are extracted into the oil, and as shown for DBCM these levels are maintained for extended periods of time when stored at either room temperature (RT) or at 4° C. (Fridge).

In one embodiment the anti-methanogenic agent is selected from the group consisting of bromochloroacetic acid (BCA), bromoform (BF), dibromoacetic acid (DBA), and dibromochloromethane (DBCM).

In one embodiment, following contacting the biomass with the at least one oil under conditions to extract at least one anti-methanogenic agent from the biomass into the at least one oil, said biomass is separated from said at least one oil. Separation of biomass from the at least one oil may be effected by any means known in the art. Means for separation include but are not limited to centrifugation, decanting, filtration, distillation, or use of a separating funnel or other equivalent means.

The amounts of biomass and at least one oil that are contacted can be varied so as to alter the amount of the at least one bioactive extracted into the at least one oil.

Figure 8:
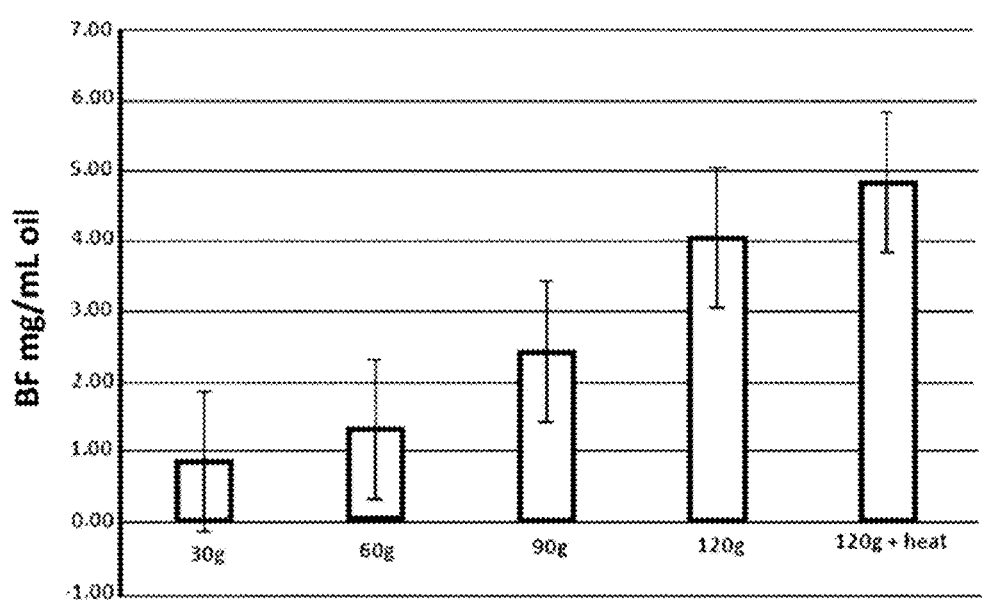
FIG. 8 shows the amount of a bioactive, bromoform (an anti-methanogenic agent) extracted into oil, using varying amounts of biomass homogenised into the same volume of oil. Heating of gelatinous samples aided the partitioning of the bioactive into the oil fraction that could be separated from the gel. Data are presented as mean #se, n=3.
Figure 9:
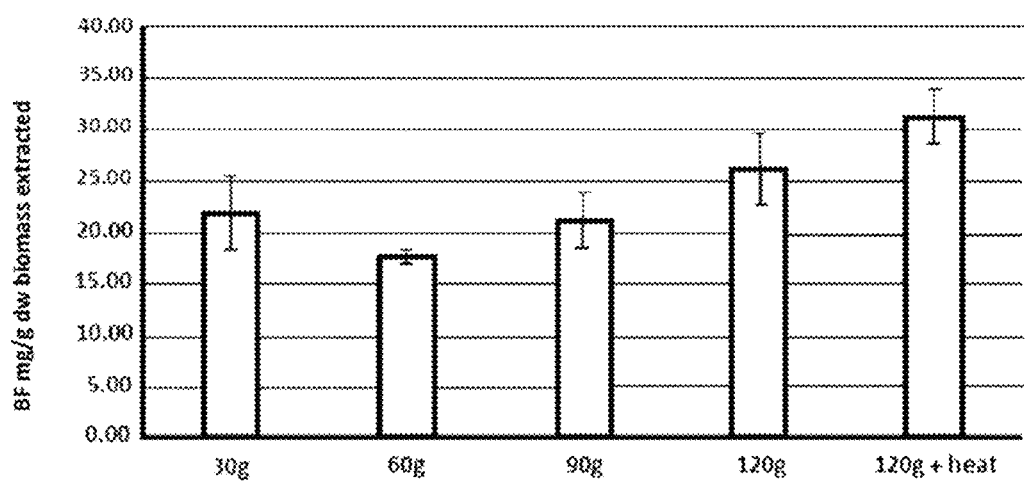
FIG. 9 shows the levels (mg/g dw biomass) of a bioactive, bromoform (an anti-methanogenic agent) in compositions prepared by extracting a biomass of *Asparagopsis* into oil by homogenising the biomass of *A. taxiformis* in oil, using varying amounts of biomass homogenised into the same volume of oil. Heating of gelatinous samples aided the partitioning of bioactive into the oil fraction that could be separated from the gel. Data are presented as mean+se, n=3.

The present inventors have also demonstrated that the amounts of at least one bioactive may be controlled by changing the ratio of biomass of *Asparagopsis* to the at least one oil. For example, FIGS. 8 and 9 show that the levels of bromoform can be increased by increasing the ratio of biomass of *Asparagopsis* to the ratio of the at least one oil.

Accordingly, in some embodiments the ratio of biomass to the at least one oil may be selected from the group consisting of 0.01 g: 1 mL, 0.05 g: 1 mL, 0.1 g: 1 mL, 0.2 g: 1 mL, 0.3 g: 1 mL, 0.4 g: 1 mL, 0.5 g: 1 mL, 0.6 g: 1 mL, 0.7 g: 1 mL, 0.8 g: 1 mL, 0.9 g: 1 mL, 1 g: 1 mL, 1.1 g: 1 mL, 1.2 g: 1 mL, 1.3 g: 1 mL, 1.4 g: 1 mL, and 1.5 g: 1 mL. Preferably, the ratio of biomass to the at least one oil is selected from the group consisting of greater than 0.3 g: 1 mL, greater than 0.6 g: 1 mL, greater than 0.9 g: 1 mL, and greater than 1.2 g: 1 mL.

In one embodiment of the invention there is provided an *Asparagopsis* oil composition prepared by the processes described herein.

The present inventors have shown previously that freeze dried, milled *Asparagopsis* species can effectively reduce total gas production and methane production in vivo in cattle, relative to a positive control of decorticated cottonseed (DCS). Importantly, decorticated cottonseed is used as a feed supplement for cattle because it considerably reduces $CH_4$ production compared to other high energy grains. The reduction in total gas production, compared to DCS, was similar among species, indicating macroalgae such as *Asparagopsis* reduce ruminant TGP and $CH_4$ production relative to high energy grains, and some macroalgae reduce ruminant TGP and $CH_4$ production relative to the DCS positive control. Furthermore, the present inventors have shown $CH_4$ production generally followed the same pattern as TGP.

Accordingly, in one embodiment the *Asparagopsis* oil composition produced by the processes described herein can be used to reduce total gas produced and/or methane produced by a ruminant animal.

Therefore, in one aspect, the invention relates to a method for reducing total gas production and/or methane production in a ruminant animal comprising the step of administering to said ruminant animal an effective amount of an *Asparagopsis* oil composition of the present invention.

In preferred embodiments of the invention, the amount of total gas produced is reduced by at least 90%, 80%, 70%, 60%, 50%, 40%, 30%, 20% or 10% compared to a reference. In one embodiment the reference is the amount of total gas produced when animals are not administered an effective amount of an *Asparagopsis* oil composition as described herein. In another embodiment, the reference is the amount of total gas produced when animals are administered decorticated cottonseed. In another embodiment, the reference is the amount of total gas produced when decorticated cottonseed is subjected to in vitro anaerobic fermentation.

In preferred embodiments of the invention, the amount of methane produced is reduced by at least 90%, 80%, 70%, 60%, 50%, 40%, 30%, 20%, 15% or 10% compared to a reference. In one embodiment the reference is the amount of methane produced when animals are not administered an effective amount of *Asparagopsis* oil composition. In another embodiment, the reference is the amount of methane produced when animals are administered decorticated cottonseed. In another embodiment, the reference is the amount of methane produced when animals are administered a pelleted commercial shipper ration based on lupins, oats, barley, wheat with cereal straw as the roughage component [chemical composition (g/kg DM) of ash, 72; crude protein (CP) 112; neutral detergent fibre (aNDFom) 519; acid detergent fibre (ADFom) 338, and free of cobalt, selenium and rumen modifiers], with an additional amount of crushed lupins referred to herein as 'a lupin diet'. In another embodiment, the reference is the amount of methane produced when a lupin diet is subjected to in vitro anaerobic fermentation.

In one embodiment, the amount of methane produced by ruminal fermentation in vitro is reduced by at least 10%, 20%, 30%, 40%, 50%, 60%, 70%, 80% or 90% compared to the amount of methane produced when decorticated cottonseed is subjected to ruminal fermentation in vitro.

In one embodiment, the amount of methane produced is reduced by at least 10%, 20%, 30%, 40%, 50%, 60%, 70%, 80% or 90% compared to the amount of methane produced when a ruminant animal is administered decorticated cottonseed.

The present inventors have also previously demonstrated that air dried, milled *Asparagopsis* can effectively reduce methane production, relative to a positive control of a lupin diet in sheep.

In one embodiment, the amount of methane produced is reduced by at least 10%, 20%, 30%, 40%, 50%, 60%, 70%, 80% or 90% compared to the amount of methane produced when a ruminant animal is administered a lupin diet.

By "effective amount", is meant a quantity of an *Asparagopsis* oil composition as described herein sufficient to allow improvement, e.g. reduction in the amount of methane production in comparison with a reference or control, reduction in the amount of total gas produced in comparison with a reference or control, maintenance of an effective level of one or more desirable volatile fatty acids in comparison with a reference or control, reduction in the acetate to propionate ratio in comparison with a reference or control, maintenance of liveweight, dry matter intake and/or organic matter intake in comparison with a reference or control. Within the meaning of the present invention, the methane reductive effect can be measured in the rumen with an artificial rumen system, such as that described in T. Hano, *J. Gen. Appl. Microbiol.*, 1993, 39, 35-45, or by in vivo oral administration to ruminants.

Therefore, in one embodiment, an *Asparagopsis* oil composition as described herein is administered at a dose equivalent to preferably at least 16.67, 10, 5, 3, 2, 1, 0.5, 0.25, 0.125 or 0.067% of the organic matter administered to the ruminant animal.

To calculate the volume of oil required to achieve a dose equivalent to a desired % level of the organic matter administered to the ruminant animal, the % organic matter amount of the *Asparagopsis* oil compositions described herein is calculated from the fresh weight (fw) of *Asparagopsis* biomass contacted with a defined volume of at least one oil. The fresh weight to dry weight (dw) ratio of blotted dry *Asparagopsis* is 10 (i.e. 30 g fw=3 g dw). Assuming a content of organic matter (OM) of 80% of dw based on previous data, the corresponding content of OM originating from *Asparagopsis* in the biomass/oil can be calculated. For example, for an *Asparagopsis* oil composition comprising 30 g fresh weight (fw) *Asparagopsis* biomass in 100 mL of at least one oil is equivalent to 0.024 *Asparagopsis* organic matter/mL. If the desired level of inclusion in feed is 0.1% *Asparagopsis* OM in 100 g feed, then 4.17 mL of the 30 g fw/100 mL *Asparagopsis* oil composition is required per 100 g of feed.

The corresponding content of OM originating from *Asparagopsis* in the biomass/oil can be calculated from different contents of organic matter (OM) % of dw. For example, a content of organic matter (OM) of 50%, 55%, 60%, 70%, 75% of dw based on previous data can be used to calculate the corresponding content of OM originating from *Asparagopsis* in the biomass/oil.

As indicated above, in a preferred embodiment, an *Asparagopsis* oil composition as described herein is administered at a dose of equivalent to preferably at least 3, 2, 1, 0.5, 0.25, 0.125 or 0.067% of the organic matter administered to the ruminant animal. Accordingly, when a 30 g fw/100 ml *Asparagopsis* oil composition as described herein is used, at least 125 mL, 83.3 mL, 41.7 mL, 20.8 mL, 10.4 mL, 5.2 mL, or 2.8 mL is required per 100 g of feed. When a 60 g fw/100 mL *Asparagopsis* oil composition as described herein is used, at least 62.5 mL, 41.7, 20.8 mL, 10.4 mL, 5.2 mL, 2.6 mL, or 1.4 mL is required per 100 g of feed. When a 120 g fw/100 mL *Asparagopsis* oil composition as described herein is used, at least 31.25 mL, 20.8 mL, 10.4 mL, 5.2 mL, 2.6 mL, 1.3 mL or 0.69 mL is required per 100 g of feed.

For example, if a 400 kg ruminant animal (e.g. steer) consumes 2.5% to 3% of its body weight per day of feed, then an *Asparagopsis* oil composition as described herein is administered at a dose proportional to the amount of organic matter administered to the ruminant. In the case of a 400 kg ruminant animal, and where 80% of the feed is organic matter, if the animal consumes about 2.5% of its body weight per day (10 kg, containing 8 kg of organic matter), 3.3 litres of a 30 g fw/100 mL *Asparagopsis* oil composition as described is required to result in a dose equivalent to 1% of the organic matter administered to the ruminant animal. 1.6 litres of a 60 g fw/100 ml *Asparagopsis* oil composition as described is required to result in a dose equivalent to 1% of the organic matter administered to the ruminant animal. 1.1 litres of a 90 g fw/100 mL *Asparagopsis* oil composition as described is required to result in a dose equivalent to 1% of the organic matter administered to the ruminant animal. 833 mL of a 120 g fw/100 mL *Asparagopsis* oil composition as described is required to result in a dose equivalent to 1% of the organic matter administered to the ruminant animal. 666 mL of a 150 g fw/100 mL *Asparagopsis* oil composition as described is required to result in a dose equivalent to 1% of the organic matter administered to the ruminant animal.

330 ml of a 30 g fw/100 mL *Asparagopsis* oil composition as described is required to result in a dose equivalent to 0.1% of the organic matter administered to the ruminant animal. 167 mL of a 60 g fw/100 ml *Asparagopsis* oil composition as described is required to result in a dose equivalent to 0.1% of the organic matter administered to the ruminant animal. 111 mL of a 90 g fw/100 mL *Asparagopsis* oil composition as described is required to result in a dose equivalent to 0.1% of the organic matter administered to the ruminant animal. 83 mL of a 120 g fw/100 ml *Asparagopsis* oil composition as described is required to result in a dose equivalent to 0.1% of the organic matter administered to the ruminant animal. 67 mL of a 150 g fw/100 mL *Asparagopsis* oil composition as described is required to result in a dose equivalent to 0.1% of the organic matter administered to the ruminant animal.

To calculate the composition including biomass required to achieve a dose equivalent to a desired % level of the organic matter administered to the ruminant animal, the % organic matter amount of the *Asparagopsis* oil compositions described herein is calculated from the fresh weight (fw) of *Asparagopsis* biomass contacted with a defined volume of at least one oil. The fresh weight to dry weight (dw) ratio of blotted dry *Asparagopsis* is 10 (i.e. 30 g fw=3 g dw). Assuming a content of organic matter (OM) of 80% of dw based on previous data, the corresponding content of OM originating from *Asparagopsis* in the biomass/oil can be calculated. For example, for an *Asparagopsis* composition comprising 30 g fresh weight (fw) *Asparagopsis* biomass in 100 mL of at least one oil is equivalent to 0.024 *Asparagopsis* organic matter/mL, and the amount of organic matter in the total final volume is calculated and included in the calculation.

An effective amount of an *Asparagopsis* oil composition as described herein may be determined by the methods described herein, including the in vitro and in vivo dose-response studies described herein. For example, the present inventors have demonstrated that ruminal fermentation in vitro can be used to examine the effect of amounts of freeze dried milled *Asparagopsis* on levels of volatile fatty acids, including acetate and propionate, methane production, and total gas production. Therefore, ruminal fermentation in vitro can be used to characterize doses of an *Asparagopsis* oil composition as described herein that may be an effective amount sufficient to allow improvement, e.g. reduction in the amount of methane production in comparison with a reference or control, reduction in the amount of total gas produced in comparison with a reference or control, maintenance of an effective level of one or more desirable volatile fatty acid in comparison with a reference or control, or reduction in the acetate to propionate ratio in comparison with a reference or control.

A ruminant is a mammal of the order Artiodactyla that digests plant-based food by initially softening and partially fermenting it within the animal's first stomach chambers, then regurgitating the semi-digested mass, now known as cud, and chewing it again.

The process of rechewing the cud to further break down plant matter and stimulate digestion is called "ruminating". Ruminants have a digestive tract with four chambers, namely the rumen, reticulum, omasum and abomasum. In the first two chambers, the rumen and the reticulum, the food is mixed with saliva and separates into layers of solid and liquid material. Solids clump together to form the cud, or bolus. The cud is then regurgitated, chewed slowly to completely mix it with saliva, which further breaks down fibers. Fiber, especially cellulose, is broken down into glucose in these chambers by symbiotic anaerobic bacteria, protozoa and fungi. The broken-down fiber, which is now in the liquid part of the contents, then passes through the rumen into the next stomach chamber, the omasum. The food in the abomasum is digested much like it would be in the monogastric stomach. Digested gut contents are finally sent to the small intestine, where the absorption of the nutrients occurs. Almost all the glucose produced by the breaking down of cellulose is used by the symbiotic bacteria. Ruminants get their energy from the volatile short chain fatty acids (VFAs) produced by the bacteria, namely acetate, propionate, butyrate, valerate, and isovalerate.

Importantly, the inventors have shown that freeze dried milled *Asparagopsis* possess the property of reducing total gas production and/or methane production in ruminant animals without compromising rumen fermentation.

For example, the inventors have shown that freeze dried milled *Asparagopsis* possess the property of reducing total gas production and/or methane production in ruminant animals without compromising rumen fermentation, for example, while maintaining an effective level of one or more desirable volatile fatty acid. The inventors have also shown that freeze dried milled *Asparagopsis* possess the property of reducing total gas production and/or methane production in ruminant animals without compromising rumen fermentation, for example, while not significantly affecting daily feed intakes and/or animal liveweight.

As used herein, the term "maintenance of an effective level", means an amount of substance in an animal or animals following treatment (e.g. administration of an *Asparagopsis* oil composition as described herein) does not significantly differ from a control or reference, including the amount of substance in an animal or animals not administered an *Asparagopsis* oil composition of the present invention.

For example, an "effective level of a desirable volatile fatty acid" is intended to mean that a quantity of a desirable volatile fatty acid is sufficient to allow improvement in a condition such as reduction in the amount of methane production in comparison with a reference or control; reduction in the amount of total gas produced in comparison with a reference or control; reduction in the acetate to propionate ratio in comparison with a reference or control; or maintenance of liveweight, dry matter intake and/or organic matter intake in comparison with a reference or control.

Carbohydrate metabolism provides energy for the growth of rumen microbes primarily through the fermentation of cellulose and starch. The insoluble polymers are converted to oligosaccharides and soluble sugars by extracellular enzymes from the rumen microorganisms. The resulting sugars are then fermented to one of various forms of volatile fatty acids, carbon dioxide and hydrogen. As used herein, the volatile fatty acids—acetic acid, propionic acid and butyric acid—are also referred to as acetate, propionate and butyrate, respectively.

Volatile fatty acids are utilized by the animal as primary carbon and energy sources with varying degrees of efficiency. High levels of propionic acid are desirable because propionic acid is a primary metabolic precursor for gluconeogenesis in the animal. The fermentation of 6-carbon sugars to acetic acid is relatively inefficient since in this process, carbon and hydrogen are lost via eructation in the form of carbon dioxide or importantly, methane. On the other hand, the production of propionic acid utilizes hydrogen and does not result in a loss of carbon or methane.

It becomes possible then to improve feed utilization efficiency and/or the rate of growth of ruminant animals by increasing the molar proportion of propionic acid relative to acetic acid, or in another embodiment, by increasing total volatile fatty acid concentration (i.e. the sum of acetic, propionic and butyric acids) in the rumen.

The present inventors have demonstrated a reduction of total gas produced and/or methane produced in anaerobic fermentation in vitro and in vivo in the presence of freeze dried milled *Asparagopsis*, without negatively affecting total VFA production in cattle. Importantly, the present inventors have shown *Asparagopsis* does not reduce the amount of VFAs in cattle; at doses of *Asparagopsis* that do not reduce the amount of organic matter or dry matter intake/degradation; at doses that decrease the acetate to propionate ratio; at doses that decrease the amount of acetate; at doses that increase the amount of propionate; and/or at doses of *Asparagopsis* that inhibit total gas and methane production, in vitro and in vivo.

Importantly, the present inventors have demonstrated freeze dried milled *Asparagopsis* does not reduce the amount of VFAs at doses of *Asparagopsis* that inhibit total gas and methane production in cattle. The present inventors have also shown freeze dried milled *Asparagopsis* does not reduce the amount of organic matter or dry matter intake/degradation in sheep; at doses that decrease the acetate to propionate ratio; at doses that decrease the amount of acetate; at doses that increase the amount of propionate; and/or at doses of *Asparagopsis* that inhibit methane production, in vitro and in vivo. For example, the present inventors have shown freeze dried milled *Asparagopsis* does not reduce the amount of organic matter or dry matter intake/degradation in sheep fed 1.2 times maintenance energy.

Therefore, in one aspect, the invention relates to a method for reducing total gas production and/or methane production in a ruminant animal comprising the step of administering to said ruminant animal an effective amount of an *Asparagopsis* oil composition of the present invention, wherein effective levels of desirable volatile fatty acids are maintained.

In one embodiment, the desirable volatile fatty acids are acetate and propionate.

As used herein, the term "volatile fatty acids" ("VFA") includes the end product of anaerobic microbial fermentation of feed ingredients in the rumen. The common VFAs include acetate, propionate, butyrate, isobutyrate, valerate, and isovalerate. The VFAs are absorbed by the rumen and used by the animal for energy and lipid synthesis.

In preferred embodiments of the invention, the total VFA produced in ruminal fermentation in the presence of an effective amount of an *Asparagopsis* oil composition as described herein is at least 80 mmol/L.

In other embodiments of the invention, the total VFA produced in ruminal fermentation in the presence of an effective amount of an *Asparagopsis* oil composition as described herein is at least 65 mmol/L.

The present inventors have also demonstrated that freeze dried, milled *Asparagopsis* does not reduce the amount of VFAs in cattle at doses of freeze dried, milled *Asparagopsis* that do not reduce the amount of organic matter or dry matter degraded from ruminal fermentation, or dry matter intake. The present inventors have also demonstrated that freeze dried, milled *Asparagopsis* does not reduce the amount of dry matter intake or liveweight of sheep. For example, the present inventors have demonstrated that freeze dried, milled *Asparagopsis* does not reduce the amount of dry matter intake or liveweight of sheep fed at 1.2 times maintenance energy. This indicates that red marine macroalgae such as *Asparagopsis* reduce total gas production and/or methane production in ruminant animals without compromising rumen fermentation.

Therefore, in one aspect, the invention relates to a method for reducing total gas production and/or methane production in a ruminant animal comprising the step of administering to said ruminant animal an effective amount of an *Asparagopsis* oil composition as described herein. In one embodiment, the effective level of a desirable volatile fatty acid is maintained. In another embodiment a ratio of acetate to propionate is decreased. In another embodiment, the level of organic matter and/or dry matter degraded is maintained. In another aspect, the invention relates to a method for reducing total gas production and/or methane production in a ruminant animal comprising the step of administering to said ruminant animal an effective amount of an *Asparagopsis* oil composition as described herein, wherein the amount of dry matter intake is maintained.

As used herein the terms, "organic matter" and "dry matter" means the amount of feed (on an organic or moisture-free basis, respectively) that an animal consumes in a given period of time, typically 24 hours. It is known in the art how to calculate organic matter and dry matter intake and/or degradation. For example, dry matter and organic matter may be 90% and 80% of the amount of feed, respectively.

In one embodiment, an *Asparagopsis* oil composition as described herein is administered at a dose equivalent to preferably at least 16.67, 10, 5, 3, 2, 1, 0.5, 0.25, 0.125 or 0.067% of the organic matter administered to the ruminant animal.

In a preferred embodiment an *Asparagopsis* oil composition as described herein is administered at a dose equivalent to preferably at least 3, 2, 1, 0.5, 0.25, 0.125 or 0.067% of the organic matter administered to the ruminant animal to maintain the amount of organic matter and/or dry matter degraded.

In another embodiment, both the amount of organic matter or dry matter degraded is maintained, and the effective levels of desirable volatile fatty acids are maintained.

In a preferred embodiment, an *Asparagopsis* oil composition as described herein is administered at a cose equivalent to preferably at least 3, 2, 1, 0.5, 0.25, 0.125 or 0.067% of the organic matter administered to the ruminant animal to maintain effective levels of desirable volatile fatty acids.

Importantly, the present inventors have demonstrated that freeze dried, milled *Asparagopsis* increases the amount of propionate at doses of *Asparagopsis* that inhibit total gas and methane production, and freeze dried, milled *Asparagopsis* increases the amount of propionate at doses of freeze, dried milled *Asparagopsis* that do not reduce the amount of organic matter or dry matter degraded.

Accordingly, in another aspect, the invention relates to a method for reducing total gas production and/or methane production in a ruminant animal comprising the step of administering to said ruminant animal an effective amount of an *Asparagopsis* oil composition as described herein, wherein the amount of organic matter or dry matter degraded is maintained and/or the ratio of acetate to propionate is decreased.

In a preferred embodiment, the *Asparagopsis* oil composition as described herein is administered at a dose equivalent to preferably at least 3, 2, 1, 0.5, 0.25, 0.125 or 0.067% of the organic matter administered to the ruminant animal to decrease the ratio of acetate to propionate.

In one embodiment the ratio of acetate to propionate (C2/C3 ratio) following administration of an *Asparagopsis* oil composition as described herein is not negatively affected. In another embodiment, the ratio of acetate to propionate (C2/C3 ratio) following administration of an *Asparagopsis* oil composition as described herein is reduced.

In another embodiment, the molar concentration of propionate is not negatively affected.

Rumen fermentation of low quality fibrous feeds is the major source of methane production in ruminants.

Examples of ruminants are listed below. However, preferably the *Asparagopsis* oil composition as described herein is used as an additive for foodstuffs for domesticated livestock such as cattle, goats, sheep and llamas. The present invention is particularly useful in cattle and sheep. Therefore, in one embodiment, said ruminant animal is selected from the members of the Ruminantia and Tylopoda suborders. In another embodiment, said ruminant animal is cattle or sheep. In a further embodiment, said ruminant animal is cattle.

By "administer" and "administered", is meant the action of introducing an *Asparagopsis* oil composition as described herein into the animal's gastro-intestinal tract. More particularly, this administration is an administration by oral route. This administration can in particular be carried out by supplementing the feed intended for the animal with an *Asparagopsis* oil composition as described herein, the thus supplemented feed then being ingested by the animal. The administration can also be carried out using a stomach tube or any other means making it possible to directly introduce said *Asparagopsis* oil composition as described herein into the animal's gastro-intestinal tract.

As discussed above, in preferred embodiments of the invention, an effective amount an *Asparagopsis* oil composition as described herein is at least 16.67, 10, 5, 3, 2, 1, 0.5, 0.25, 0.125 or 0.067% of the organic matter administered to the ruminant animal.

For example, an *Asparagopsis* oil composition as described herein is administered at a dose of preferably at least 3, 2, 1, 0.5, 0.25, 0.125 or 0.067% of the organic matter available in the diet of the ruminant animal.

For example, if a ruminant animal consumes approximately 2.5-3% of its live weight of feed a day, a 400 kg ruminant animal may consume 10-12 kg of feed a day. For example, if a 400 kg ruminant animal (e.g. steer) consumes 2.5% to 3% of its body weight per day of feed, then an *Asparagopsis* oil composition as described herein is administered at a dose proportional to the amount of organic matter administered to the ruminant. In the case of a 400 kg ruminant animal, and where 80% of the feed is organic matter, if the animal consumes about 2.5% of its body weight per day (10 kg, containing 8 kg of organic matter), 3.3 litres of a 30 g fw/100 mL *Asparagopsis* oil composition as described is required to result in a dose equivalent to 1% of the organic matter administered to the ruminant animal. 1.6 litres of a 60 g fw/100 mL *Asparagopsis* oil composition as described is required to result in a dose equivalent to 1% of the organic matter administered to the ruminant animal. 1.1 litres of a 90 g fw/100 mL *Asparagopsis* oil composition as described is required to result in a dose equivalent to 1% of the organic matter administered to the ruminant animal. 833 mL of a 120 g fw/100 ml *Asparagopsis* oil composition as described is required to result in a dose equivalent to 1% of the organic matter administered to the ruminant animal. 666 mL of a 150 g fw/100 mL *Asparagopsis* oil composition as described is required to result in a dose equivalent to 1% of the organic matter administered to the ruminant animal. 330 ml of a 30 g fw/100 ml *Asparagopsis* oil composition as described is required to result in a dose equivalent to 0.1% of the organic matter administered to the ruminant animal. 167 mL of a 60 g fw/100 mL *Asparagopsis* oil composition as described is required to result in a dose equivalent to 0.1% of the organic matter administered to the ruminant animal. 111 ml of a 90 g fw/100 mL *Asparagopsis* oil composition as described is required to result in a dose equivalent to 0.1% of the organic matter administered to the ruminant animal. 83 mL of a 120 g fw/100 mL *Asparagopsis* oil composition as described is required to result in a dose equivalent to 0.1% of the organic matter administered to the ruminant animal. 67 mL of a 120 g fw/100 ml *Asparagopsis* oil composition as described is required to result in a dose equivalent to 0.1% of the organic matter administered to the ruminant animal.

The effective amount can be administered to said ruminant animal in one or more doses.

The effective amount can also be administered to said ruminant animal in one or more doses on a daily basis.

The dosages defined herein as the amount per kg body weight per day concern the average amount of the *Asparagopsis* oil composition as described herein administered during a given period of treatment, e.g. during a week or a month of treatment. An *Asparagopsis* oil composition as described herein may therefore be administered every day, every other day, etc., without departing from the scope of the invention. Preferably though, the method comprises daily administration of an *Asparagopsis* oil composition as described herein in prescribed dosages. Even more preferably an *Asparagopsis* oil composition as described herein is administered during feeding of the animal each time the animal is fed, in amounts yielding the above daily dosages.

The present method may comprise administration of an *Asparagopsis* oil composition as described herein in accordance with the above described dosage regimens for a period of at least 5, 10, 25, 50, 100, 250 or 350 days. An aspect of the invention resides in the fact that the present methods provides very persistent effectiveness in reducing enteric methanogenesis, e.g. the effect does not diminish over extended periods of treatment, e.g. as a result of increasing resistance of rumen or gut microorganisms, thereby rendering long-term treatment of the ruminant particularly feasible.

Accordingly, given the significant effects of freeze dried, milled *Asparagopsis*, including reducing total gas production and $CH_4$ output, in one embodiment an *Asparagopsis* oil composition as described herein is preferably administered in a form that results in the effects described herein (e.g. to reduce $CH_4$ output) without affecting nutritionally important fermentation parameters.

Of the diversity of secondary metabolites produced by *Asparagopsis*, bromoform ($CHBr_3$) is one of the most abundant and biologically active. However, bromoform and chemically related compounds (e.g. bromochloromethane) as purified chemicals are unsafe and disallowed for human and animal applications, including the inhibition of methanogenesis in ruminant animals.

Figure 2:
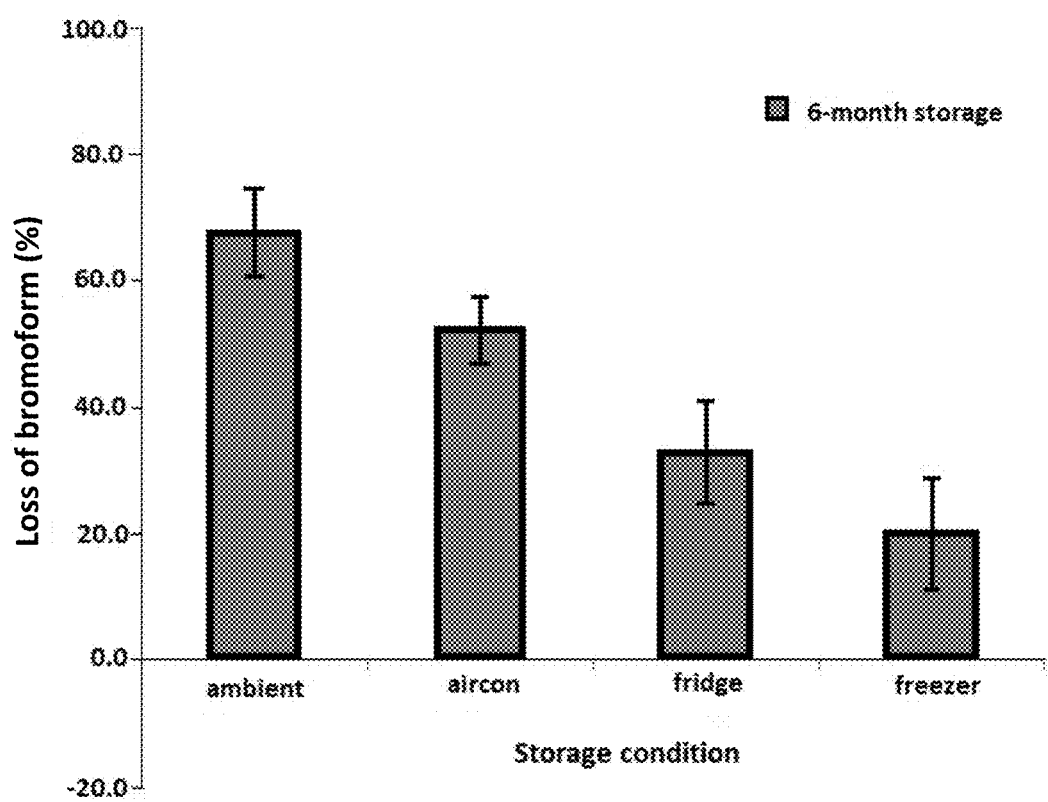
FIG. 2 shows the loss (%) of a bioactive, bromoform (an anti-methanogenic agent) from a composition when stored under different conditions over a period of 6 months: at ambient conditions (25° C.±10° C.); in an air-conditioned room; in a refrigerator at 4° C.; and in a freezer at −20° C. Data are presented as mean #se, n=3.

While intact freeze dried, milled biomass of *Asparagopsis* can be used as a feed supplement to inhibit methanogenesis in ruminants it requires careful processing prior to feeding to minimise the loss of bioactive compounds, such as bromoform, and maintain activity. The most effective current method of preparation of biomass of *Asparagopsis* is to immediately freeze and subsequently freeze dry biomass for use as a feed supplement. However, the present inventors have previously found there are major losses of bromoform if the intact biomass is not immediately frozen and/or is air dried. Furthermore, there are major losses after 6 months if the freeze dried biomass is stored under ambient temperature (66% loss), or even refrigerated conditions (32% loss), with freezing of freeze dried material (20% loss) being the only practical option for long term storage (>6 months) (FIG. 2). These processing and storage conditions have been described in Vucko et al. (J. Appl. Phycol. 2017, 29, 1577-1586).

Surprisingly, the present inventors have found that *Asparagopsis* oil compositions prepared by contacting a biomass of *Asparagopsis* with an oil, retain high levels of a bioactive for extended periods of time, even when stored at either room temperature or at 4° C. For example, as described above, FIG. 3 shows that *Asparagopsis* oil compositions prepared by contacting a biomass of *Asparagopsis* with an oil, with or without homogenisation, retain high levels of a bioactive for extended periods of time, when stored at either room temperature or at 4° C. The processes of the present invention therefore allow the production of *Asparagopsis* oil compositions in a form which is suitable for long term storage (>6 months) at room temperature.

The present invention results in a significant reduction in losses of bioactive components that would otherwise occur during transport, drying, and/or storage of biomass of *Asparagopsis* harvested from the wild. The present invention also reduces the number of steps to obtain a blended product of preserved intact biomass, or a bioactive extract, and therefore represents a substantial improvement on current processing techniques.

In another embodiment, an *Asparagopsis* oil composition as described herein is preferably administered in a form in which the secondary metabolites remain effective (e.g. therapeutically effective).

An *Asparagopsis* oil composition as described herein may be administered to the ruminant in one of many ways. An *Asparagopsis* oil composition as described herein can be administered in a solid form as a veterinary pharmaceutical, may be distributed in an excipient, and directly fed to the animal, may be physically mixed with feed material in a dry form or the *Asparagopsis* oil composition as described herein may be provided as a solution and thereafter sprayed onto feed material. The method of administration of an *Asparagopsis* oil composition as described herein to the animal is considered to be within the skill of the artisan.

When used in combination with a feed material, the feed material is preferably grain/hay/silage/grass-based. Included amongst such feed materials are improved and/or tropical grass or legume based forages either grazed directly or prepared as a conserved forage hay, any feed ingredients and food or feed industry by-products as well as bio-fuel industry by-products and corn meal and mixtures thereof, or feed lot and dairy rations, such as those high in grain content.

The time of administration is not crucial so long as the reductive effect on methane production is shown. As long as the feed is retained in the rumen, administration is possible at any time. However, since an *Asparagopsis* oil composition as described herein is preferably present in the rumen at about the time methane is produced, an *Asparagopsis* oil composition as described herein is preferably administered with or immediately before feed.

In a particular embodiment of the invention, said effective amount of an *Asparagopsis* oil composition as described herein is administered to a ruminant animal by supplementing a feed intended for said animal with said effective amount of an *Asparagopsis* oil composition as described herein. By "supplementing", within the meaning of the invention, is meant the action of incorporating the effective amount of an *Asparagopsis* oil composition as described herein directly into the feed intended for the animal. Thus, the animal, when feeding, ingests the *Asparagopsis* oil composition as described herein which can then act to increase e.g. the digestibility of the fibres and/or cereals contained in the animal's feed.

Thus, another subject of the invention relates to a feed supplement for a ruminant animal comprising an *Asparagopsis* oil composition as described herein.

In another aspect the present invention also provides a feed supplement for reducing total gas production and/or methane production in a ruminant animal, said supplement comprising an effective amount of an *Asparagopsis* oil composition as described herein.

In one embodiment, the effective amount an *Asparagopsis* oil composition as described herein is administered to said ruminant animal by supplementing food intended for said animal with said effective amount of an *Asparagopsis* oil composition as described herein.

As discussed above, in one embodiment the present invention maintains the levels of VFAs in the ruminant animal. Thus, this method allows the ruminant animal to maintain energy from feed based on e.g. fibers and cereals, and as a result, starting from the same calorific intake, to maintain the energy available for metabolism while mitigating total gas and $CH_4$ production.

This is advantageous for the livestock farmer who can thus optimize the cost of the feed per unit of metabolisable energy available. This also represents a substantial economic benefit.

The present inventors have demonstrated previously that administration of an effective amount of freeze dried, milled *Asparagopsis* to a ruminant animal does not negatively impact voluntary feed intake. Therefore, the present invention includes methods wherein the level of organic matter and/or dry matter degraded is maintained.

As used herein, the term "animal feed supplement" refers to a concentrated additive premix comprising the active ingredients, which premix or supplement may be added to an animal's feed or ration to form a supplemented feed in accordance with the present invention. The terms "animal feed premix," "animal feed supplement," and "animal feed additive" are generally considered to have similar or identical meanings and are generally considered interchangeable. Typically, the animal feed supplement of the present invention is in the form of a powder or compacted or granulated solid. In practice, livestock may typically be fed the animal feed supplement by adding it directly to the ration, e.g. as a so-called top-dress, or it may be used in the preparation or manufacture of products such as compounded animal feeds or a lick blocks, which will be described in more detail hereafter. The invention is not particularly limited in this respect. A supplement according to the invention is typically fed to an animal in an amount ranging from 16-2500 g/animal/day.

In one embodiment, a supplement according to the invention is administered at an amount based on actual individual animal intake (e.g. g/kg DM intake).

The present animal feed supplement comprises an *Asparagopsis* oil composition as described herein, and is formulated so that when added to feed, the *Asparagopsis* oil composition is present at an amount equivalent to at least 0.067, 0.125, 0.25, 0.5, 1, 2, 3, 5, 10 or 16.67% of the organic matter of the feed.

For example, if a ruminant animal consumes approximately 5 kg of organic matter a day, the animal feed supplement comprises an *Asparagopsis* oil composition as described herein and is formulated so that when added to feed, the *Asparagopsis* oil composition as described herein is administered at a dose of 208 mL per day. 208 mL of a 30 g fw/100 mL *Asparagopsis* oil composition as described is required to result in a dose equivalent to 0.1% of the organic matter administered to the ruminant animal. 104 mL of a 60 g fw/100 mL *Asparagopsis* oil composition as described is required to result in a dose equivalent to 0.1% of the organic matter administered to the ruminant animal. 52 mL of a 120 g fw/100 mL *Asparagopsis* oil composition as described is required to result in a dose equivalent to 0.1% of the organic matter administered to the ruminant animal. 2082 mL of a 30 g fw/100 ml *Asparagopsis* oil composition as described is required to result in a dose equivalent to 1% of the organic matter administered to the ruminant animal. 1041 mL of a 60 g fw/100 mL *Asparagopsis* oil composition as described is required to result in a dose equivalent to 1% of the organic matter administered to the ruminant animal. 520 ml of a 120 g fw/100 mL *Asparagopsis* oil composition as described is required to result in a dose equivalent to 1% of the organic matter administered to the ruminant animal.

In preferred embodiments of the invention, the supplement comprises an *Asparagopsis* oil composition as described herein present in an amount ranging from 10-100 wt %, preferably said amount is in excess of 10, 20, 30, 40, 50, 60, 70, 80, 90, 95, 97 or 99 wt %.

It is within the skills of the trained professional to determine exactly the ideal amounts of the components to be included in the supplement and the amounts of the supplement to be used in the preparation of the ration or compounded animal feed, etc., taking into account the specific type of animal and the circumstances under which it is held. Preferred dosages of each of the components are given herein.

The animal feed supplements of the present invention may comprise any further ingredient without departing from the scope of the invention. It may typically comprise well-known excipients that are necessary to prepare the desired product form and it may comprise further additives aimed at improving the quality of the feed and/or at improving the performance of the animal consuming the supplement. Suitable examples of such excipients include carriers or fillers, such as lactose, sucrose, mannitol, starch crystalline cellulose, sodium hydrogen carbonate, sodium chloride and the like and binders, such as gum arabic, gum tragacanth, sodium alginate, starch, PVP and cellulose derivatives, etc. Examples of feed additives known to those skilled in the art include vitamins, amino acids and trace elements, digestibility enhancers and gut flora stabilizers and the like.

The present inventors have demonstrated freeze dried, milled *Dictyota, Oedogonium,* and *Cladophora patentiramea* reduce total gas production and $CH_4$ production from ruminal fermentation. Therefore, in another embodiment, the methods further comprise administering to said ruminant animal an effective amount of at least one species of macroalgae selected from the group consisting of *Asparagopsis armata, Asparagopsis taxiformis, Dictyota* spp (e.g. *Dictyota bartayresii*), *Oedogonium* spp, *Ulva* spp, and *C. patentiramea*.

Accordingly, in one aspect the present invention relates to a method for reducing total gas production and/or methane production in a ruminant animal comprising the step of administering to said ruminant animal an effective amount *Asparagopsis* oil composition as described herein and a composition comprising marine macroalgae, or marine macroalgae oil extract.

In one embodiment the marine macroalgae of the composition is selected from the group consisting of *Asparagopsis armata*, *Asparagopsis taxiformis*, *Dictyota* spp (e.g. *Dictyota bartayresii*), *Oedogonium* spp, *Ulva* spp, and *C. patentiramea*.

A further aspect of the invention concerns products such as a compounded animal feeds and lick blocks, comprising a supplement as defined herein before.

The term 'compounded animal feed composition' as used herein, means a composition which is suitable for use as an animal feed and which is blended from various natural or non-natural base or raw materials and/or additives. Hence, in particular, the term 'compounded' is used herein to distinguish the present animal feed compositions from any naturally occurring raw material. These blends or compounded feeds are formulated according to the specific requirements of the target animal. The main ingredients used in commercially prepared compounded feeds typically include wheat bran, rice bran, corn meal, cereal grains, such as barley, wheat, rye and oat, soybean meal, alfalfa meal, cottonseed meal, wheat powder and the like. A commercial compound feed will typically comprise no less than 15% of crude protein and no less than 70% digestible total nutrients, although the invention is not particularly limited in this respect. Liquid, solid as well as semi-solid compounded animal feed compositions are encompassed within the scope of the present invention, solid and semi-solid forms being particularly preferred. These compositions are typically manufactured as meal type, pellets or crumbles. In practice, livestock may typically be fed a combination of compounded feed, such as that of the present invention, and silage or hay or the like. Typically a compounded animal feed is fed in an amount within the range of 0.3-10 kg/animal/day. It is within the skills of the trained professional to determine proper amounts of these components to be included in the compounded animal feed, taking into account the type of animal and the circumstances under which it is held.

The compounded animal feed compositions of the invention may comprise any further feed additive typically used in the art. As is known by those skilled in the art, the term 'feed additive' in this context refers to products used in animal nutrition for purposes of improving the quality of feed and the quality of food from animal origin, or to improve the animals' performance, e.g. providing enhanced digestibility of the feed materials. Non-limiting examples include technological additives such as preservatives, antioxidants, emulsifiers, stabilising agents, acidity regulators and silage additives; sensory additives, especially flavours and colorants; (further) nutritional additives, such as vitamins, amino acids and trace elements; and (further) zootechnical additives, such as digestibility enhancers and gut flora stabilizers.

As will be clear to those skilled in the art, the present compounded animal feed compositions can comprise any further ingredient or additive, without departing from the scope of the invention.

In a further aspect, the invention provides a lick stone or lick block comprising an *Asparagopsis* oil composition as described herein. As is known to those skilled in the art such lick stones or blocks are particularly convenient for feeding mineral supplements (as well as proteins and carbohydrates) to ruminants grazing either or both natural and cultivated pastures. Such lick blocks or lick stones in accordance with the present invention typically comprise, in addition to an *Asparagopsis* oil composition as described herein, various types of binders, e.g. cements, gypsum, lime, calcium phosphate, carbonate, and/or gelatin; and optionally further additives such as vitamins, trace elements, mineral salts, sensory additives, etc.

A further aspect of the invention concerns a method of reducing gastro-intestinal methane production in a ruminant, said method comprising administering a composition comprising an *Asparagopsis* oil composition as described herein.

The term 'reducing gastro-intestinal methanogenesis' and 'reducing gastro-intestinal methane production' as used herein refers to the reduction of methane gas production in the gastro-intestinal tract. As explained hereinbefore, fermentation in the rumen and the gut of a ruminant gives rise to production of methane gas by so-called methanogens. The present invention aims to reduce this process, such as to reduce the methane excretion directly from the gastro-intestinal tract. It is within the knowledge and skill of those trained in the art to assess methane excretion by an animal. As explained before, methane production in the rumen and gut is a process normally occurring in healthy animals and decreasing methanogenesis does not enhance or diminish the ruminant's general state of health or well-being.

Thus, the present methods of treatment are non-therapeutic methods of treatment, i.e. the methods do not improve the health of an animal suffering from a particular condition, do not prevent a particular disease or condition, nor do they to any extent affect the health of the ruminant in any other way, i.e. as compared to a ruminant not receiving the present methods of treatment. The advantages of the present methods are limited to environmental and/or economic aspects as explained before.

As will be clear from the above, the present method comprises oral administration of an *Asparagopsis* oil composition as described herein. Preferably the treatment comprises oral administration of the compounded animal feed compositions and/or the animal feed supplement products as defined hereinbefore, even though other liquid, solid or semi-solid orally ingestible compositions may be used without departing from the scope of the invention, as will be understood by those skilled in the art.

In accordance with the foregoing, still a further aspect of the invention concerns the use of a composition comprising an *Asparagopsis* oil composition as described herein for the non-therapeutic reduction of gastro-intestinal methane production in a ruminant.

In another aspect, the present invention also provides a feed for a ruminant animal, wherein said feed is supplemented with a feed supplement described herein.

In another aspect the present invention provides a method for reducing methane production by a ruminant animal, said method comprising the step of administering to said animal a feed supplement described herein or a feed described herein.

As used herein the term "shelf life" is used to indicate that the amount or level of a bioactive (e.g. anti-methanogenic) agent in the at least one oil is not significantly reduced for the period of time and temperature that the composition is stored at. In other words, the amount of time elapsed before there is a significant reduction in the level of a bioactive (e.g. anti-methanogenic) agent is taken to indicate the shelf life. The term "stability" is also used as an indicator of shelf life. The 'stability' of at least one bioactive (e.g. anti-methanogenic) agent can be assessed by measuring the level of the anti-methanogenic agent over time.

The level of the bioactive (e.g. anti-methanogenic) agent will typically decrease over time once it has been extracted into an oil, and this will be dependent upon storage conditions. The decrease in level may be due to many reasons, such as evaporation or sublimation of the bioactive (e.g. anti-methanogenic) agent from the oil. It may also be due to reaction of the bioactive (e.g. anti-methanogenic) agent with either itself, residual water in the oil extract, oxygen or other gases in the air, other components in the oil, or reaction with the oil itself, and may be mediated by light and/or heat, as is typical of many halogenated compounds. The level that the bioactive (e.g. anti-methanogenic) agent is reduced by, to still be acceptable for consumption will vary depending upon a number of factors, such as the end use of the product and the decomposition by-products which may be produced. For example, the level that the at least one bioactive (e.g. anti-methanogenic) agent may be reduced by may be no more than 5%, 10%, 20%, 30%, 40%, or 50%, following storage at either 4° C. or 25° C., and this will still be acceptable for use. In one embodiment, the level of the at least one bioactive (e.g. anti-methanogenic) agent may be reduced by no more than 20% after 65 weeks of storage at 25° C. In another embodiment, the level of the at least one anti-methanogenic agent may be reduced by no more than 50% after 65 weeks of storage at either 4° C. or 25° C.

ABBREVIATIONS

A number of abbreviations are used throughout the specification. For the avoidance of doubt, these abbreviations are defined below:
ANOVA analysis of variance
BCA bromochloroacetic acid
BF bromoform
d day(s)
DBA dibromoacetic acid
DBCM dibromochloromethane
DCM dichloromethane
dw dry weight
eq. equivalent(s)
fw fresh weight
GC gas chromatography
HPLC high performance/pressure liquid chromatography
IS internal standard
MS mass spectrometry
MTBE methyl tert-butyl ether
n number of samples
OM organic matter
RT room temperature
VFA volatile fatty acid(s)
wk week(s)
The invention will now be further described by way of Examples, which are meant to serve to assist one of ordinary skill in the art in carrying out the invention and are not intended in any way to limit the scope of the invention.

EXAMPLES

Example 1: Preparation of *Asparagopsis* Oil Compositions

*Asparagopsis taxiformis* (gametophyte stage) was collected from Magnetic Island (QLD, Australia). *Asparagopsis armata* is collected from Cloudy Bay, Bruny Island, Tasmania, 43°.43'94" S; 147°.21'.52" E. Fresh biomass was blotted dry and samples (6×30.0 g fresh weight (fw)) were collected into separate 250 mL glass bottles (Schott), each pre-filled with 100 ml of vegetable oil (Homebrand blended vegetable oil, canola oil 95%, sunflower oil 5%). Comparative samples (6×30.0 g fresh weight (fw)) were also collected into 100 mL of milliQ water instead of vegetable oil.

All bottles were securely capped and stored on ice for immediate transport to the laboratory for further processing.
Samples of biomass (6×30.0 g fw) were also collected into zip lock bags for determination of dry weight (dw), and to determine bromoform content in the biomass (3×30.0 g fw).

In the laboratory (less than 4 h from time of collection), the biomass in each solvent (oil or water) was homogenised by shredding using an IKA ultra-turrax T-25, for 60 s (n=3 for oil and n=3 for water), with the biomass in the remaining three replicates for each solvent kept intact. All bottles with biomass (n=12) were then stored in a refrigerator (4° C.). The samples were analysed for bromoform content, being representative of anti-methanogenic agents present in the algae, on days 1, 3, 5, 7, and 10 after collection (day 0).

For analysis of bromoform, 1.5 mL of the extraction solvent (oil or water) was collected from each replicate bottle and centrifuged (12 000 g, 1 min) to remove solids. Bromoform (BF) was extracted from 1.0 mL of the resulting clarified solutions, using either methyl tert-butyl ether (MTBE) or methanol, as described below.

For samples using water as solvent, bromoform was extracted from the 1.0 mL subsamples from each replicate bottle using 1.0 mL of a naphthalene-ether solution (10 µg·mL$^{-1}$ of naphthalene in methyl tert-butyl ether (MTBE)). The naphthalene served as an internal standard and the MTBE was the extraction solvent. The MTBE phase was collected and analysed by GC/MS as described below.

For samples using oil as a solvent, bromoform was extracted from the 1.0 ml subsamples from each replicate bottle using 1.0 mL of a naphthalene-methanol solution (10 µg·mL$^{-1}$ of naphthalene in HPLC-grade methanol). Samples were allowed to partition for 2 hours at 4° C. prior to analysis of the methanol layer. The partitioning conditions were selected based on previous experiments using different solvents (hexane, methanol, MTBE, DCM) and time periods (from 30 min to 48 h). The methanol phase was collected and analysed by GC/MS as described below.

Figure 10:
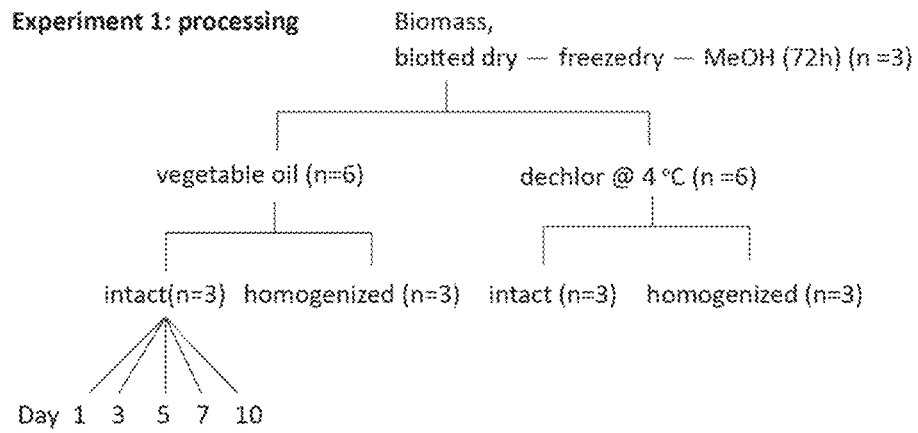
FIG. 10 shows the experimental design for the extraction of halogenated metabolites from intact or homogenized biomass of *A. taxiformis* into oil or water is shown below, as described in Example 1.

The experimental design for the extraction of halogenated metabolites from intact or homogenized biomass of *A. taxiformis* into oil or water is shown in FIG. 10.

For determination of dry weight and content of bromoform, biomass was immediatedly frozen and then freeze-dried (Virtiz benchtop 2K, −55° C., 120 ubar, 48 h). The dried biomass was weighed to determine the dry weight, then milled to 1 mm particles, and stored at −20° C. in sealed jars.

Bromoform was quantified by GC/MS (Agilent 7890c equipped with a Zebron ZB-wax capillary column, 30 m×0.25 mm×0.25 µm, Phenomenex, Australia) following Paul et al. (Mar. Ecol. Prog. Ser., 306 (2006) 87-101) with modifications as described in Machado et al. (J Appl Phycol, 28 (2016) 3117-3126). Briefly, the analytical conditions were pulsed injections (1 µL, 35 psi) in splitless mode, with the following temperature parameters: injection port (250° C.), GC/MS interface (300° C.), and oven (held at 40° C. for 1 min, ramped at 16° C.·min$^{-1}$ to 250° C., then held at 250° C. for 2 min), as described by Paul et al. Helium was used as the carrier gas at 2 mL·min$^{-1}$. Separate standard curves were completed for each method (aqueous, oil, biomass) and the concentration of target compounds in each sample was calculated from the ratio of the peak areas of target compound over the internal standard. Bromoform was identified by comparison with a commercial standard (Sigma Aldrich, Australia) and based on its characteristic ion fragments (molecular ion cluster at m/z 250, 252, 254, 256 [1:2:2:1]). The concentration of bromoform in the solutions was normalised to the amount of dry biomass extracted and reported as mg bromoform/g dw biomass.

The dry weight of a 30 g sample of blotted dry *Asparagopsis* was determined to be about 3 g. FIG. 1 shows the results from the different extraction methods (using water as a solvent vs oil as a solvent; and using intact biomass vs homogenised/shredded biomass), wherein the biomass is contacted with the solvent (water or oil) for a period of time of up to 10 days. The results are plotted as amount of BF extracted (mg) per gram of dry weight of algae. BF was also extracted using a previously described method, for comparison. This method involved freeze-drying the biomass sample and extracting the BF into methanol by contacting the biomass with the methanol for 72 hours.

FIG. 1 shows *Asparagopsis* biomass extracted with water yielded less BF than *Asparagopsis* biomass extracted with oil; the level of the BF extracted from the *Asparagopsis* biomass into the oil is increased relative to the level of the BF extracted from an equivalent amount of biomass into water. This data demonstrates the extraction of BF, a bioactive agent, from biomass of *Asparagopsis* into an oil, to form an *Asparagopsis* oil composition.

When used as an extraction solvent, intact or homogenised biomass gave similar results. The amount of BF extracted from these samples was approximately 50% lower than with using oil as a solvent (after 24 h), and remained approximately 30-40% lower for the duration of the steeping time (up to day 10).

FIG. 1 also shows homogenising the biomass in the oil resulted in the highest amount of bromoform extracted in the shortest amount of time (day 1), with BF content of intact biomass in oil reaching similar levels to homogenised biomass only after about seven days of steeping/extraction. This data demonstrates the speed of extraction of BF, a bioactive agent, from biomass of *Asparagopsis* into an oil, is increased by homogenising the biomass in the at least one oil.

FIG. 1 also shows that the extraction efficiency by use of oil was dependent on whether biomass was intact or homogenised. Surprisingly, homogenised biomass extracted with oil yielded much more BF, even after 24 h, compared to methods of extracting freeze-dried biomass with methanol for 72 h. As can be seen from FIG. 1, a freeze-dried sample extracted by steeping in methanol for 72 h only gave about 15 mg of BF/g algae (dw), whereas a homogenised sample of algae, steeping for only 24 h in oil, gave about 17.8 mg of BF/g algae (dw), which represents a significant improvement over extracting freeze-dried biomass with methanol. This data demonstrates the level of extraction of BF, a bioactive agent, from biomass of *Asparagopsis* into an oil, is increased by homogenising the biomass in the at least one oil.

Example 2: Shelf Life of *Asparagopsis* Oil Compositions

The shelf life (e.g. stability) of the *Asparagopsis* oil compositions of the present invention was assessed. The ratio of bioactive compounds such as bromoform (BF) and dibromochloromethane (DBCM), were examined and compared to an internal standard (IS; naphthalene), as a function of time. Any reduction in the ratio indicates a loss of a compound and therefore decreased stability of the bioactive oil compositions, resulting in shortened shelf-life.

Figure 11:
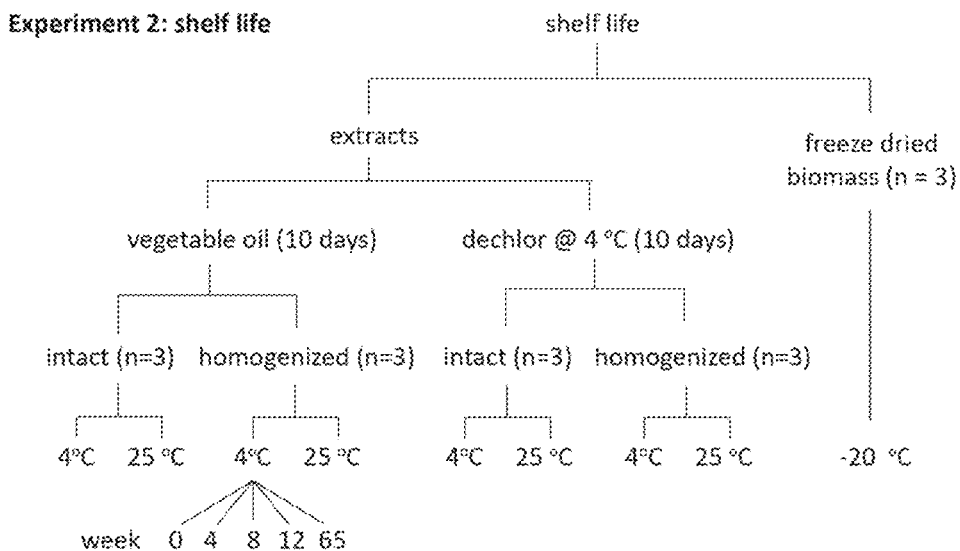
FIG. 11 shows the experimental design for the assessment of shelf life of the *Asparagopsis* oil compositions of the present invention, as described in Example 2.

After 10 days of extracting *Asparagopsis* biomass into oil or water, biomass was removed. The *Asparagopsis* oil compositions (with biomass) were filtered through a 100 µm nylon mesh followed by centrifugation (3200 g, 15 min). The clarified solution from each replicate of each treatment (oil or water) was then split into two 30 mL glass bottles (Schott), with one of these bottles stored at 4° C. and the other at 25° C. (n=3 per temperature, total of 24 bottles). Subsamples (1 mL) were collected after 0, 4, 8, 12, and 65 weeks of storage and analysed as described above. Week 0 was counted from the day storage was initiated, as shown in the Experimental Design of FIG. 11.

Freeze dried biomass was also analysed for the content of bromoform at the same time intervals, with week 0 counted from day of removal of the biomass from the freeze dryer.

Freeze-dried biomass stored at −20° C. in accordance with the standard storage method showed no losses with time using the standard methanol extraction method (data not presented).

FIG. 3 shows the stability of the *Asparagopsis* oil compositions of the present invention over time. As can be seen for the water extracts, there were significant losses of a bioactive, bromoform, by 12 weeks of storage at both 4° C. and 25° C. Water samples were therefore not analysed further for these samples.

In contrast, the level of a bioactive, bromoform, extracted into oil, for either treatment (homogenised or intact), did not significantly reduce over 12 weeks, regardless of whether storage was at 4° C. or 25° C. (FIG. 3). Surprisingly, after 65 weeks there was no significant decrease of bromoform in *Asparagopsis* oil compositions stored at 4° C. for either treatment (homogenised or intact). *Asparagopsis* oil compositions stored at 25° C. for 65 weeks had lost 15 to 20% of the original bromoform extracted. The apparent 'gain' of BF over time can be ascribed to analytical variance. This data demonstrates *Asparagopsis* oil compositions formed by the extraction of *Asparagopsis* into an oil are stable over extended periods of time. In particular, this data demonstrates the levels of a bioactive, BF, in *Asparagopsis* oil compositions formed by the extraction of *Asparagopsis* into an oil are stable over extended periods of time.

Figure 4:
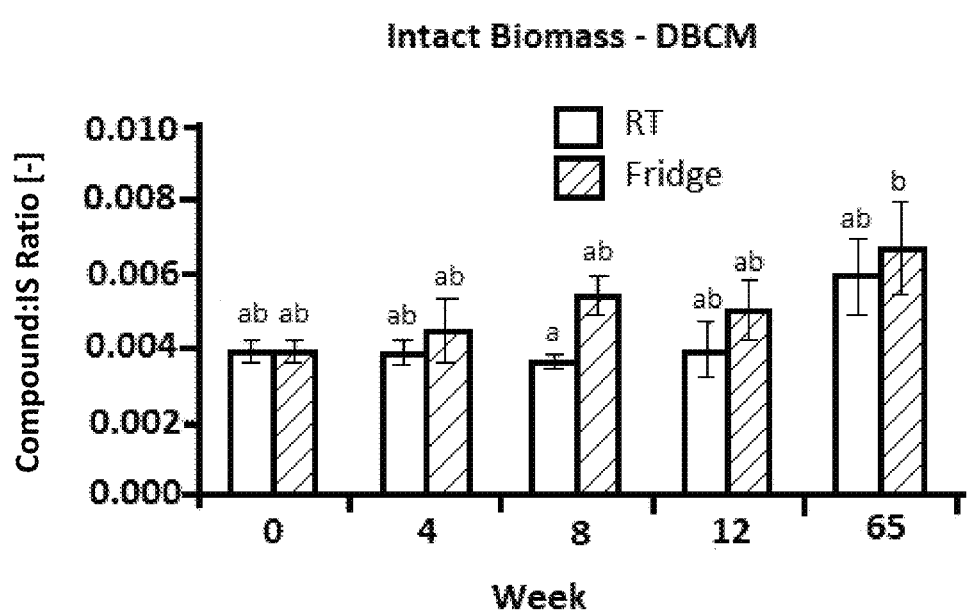
FIG. 4 shows the retention of a bioactive, DBCM (an anti-methanogenic agent) in compositions prepared by extracting intact biomass of *Asparagopsis* into oil, at t=0 and after 4, 8, 12, and 65 weeks of storage (at either 4° C.; "Fridge", or 25° C.; "RT"). Shown is the ratio of DBCM: naphthalene (IS) in oil. Bars with the same superscript letters are not significantly different. Data are presented as mean+se, n=3.
Figure 5:
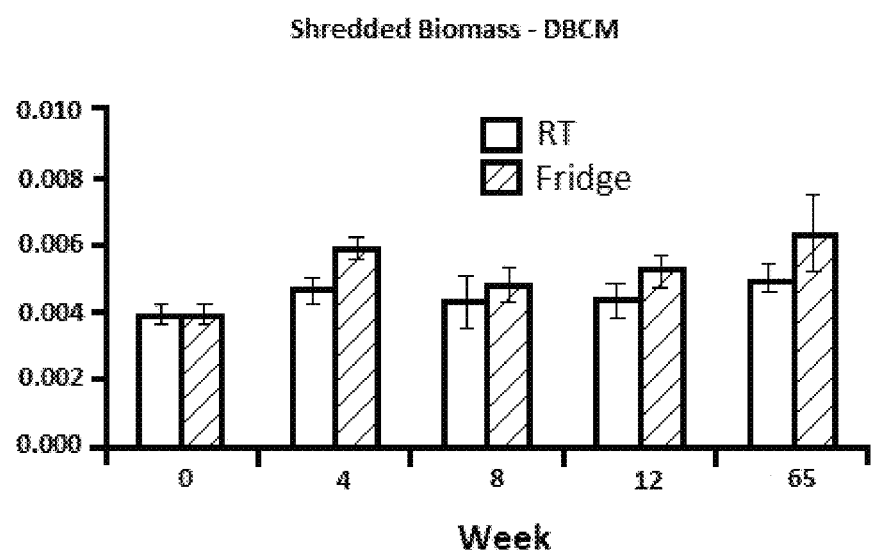
FIG. 5 shows the retention of a bioactive, DBCM (an anti-methanogenic agent) in compositions prepared by extracting a biomass of *Asparagopsis* into oil, prepared by homogenising the biomass of *A. taxiformis* in oil, at t=0 and after 4, 8, 12, and 65 weeks of storage (at either 4° C.; "Fridge", or 25° C.; "RT"). Shown is the ratio of DBCM: naphthalene (IS) in oil. Data are presented as mean+se, n=3. This data shows no statistical differences in the ratios of DBCM: IS.

The results of DBCM: IS ratio over time is shown in FIG. 4 (intact biomass) and FIG. 5 (homogenised biomass). DBCM was detected throughout the 65 week storage period. Importantly, there were no significant differences in the ratio of DBCM:IS within each treatment (intact biomass vs homogenised biomass, or storage at 4° C. vs 25° C.), demonstrating excellent shelf life for all samples, using DBCM as a marker for anti-methanogenic agents. The apparent 'gain' of DBCM: IS ratio over time can be ascribed to analytical variance. This data demonstrates the levels of DBCM in *Asparagopsis* oil compositions formed by the extraction of *Asparagopsis* into an oil are stable over extended periods of time.

Figure 6:
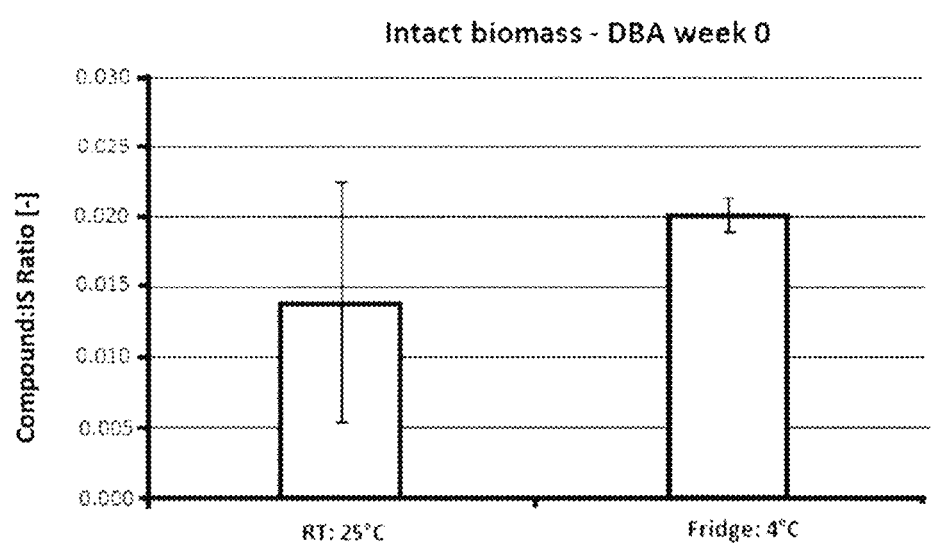
FIG. 6 shows amount of a bioactive, DBA, in compositions prepared by extracting intact biomass of *Asparagopsis* into oil for a period of 10 days followed by immediate storage (week 0) at the shown temperatures (25° C./"RT" or 4° C./"Fridge"). Shown is the ratio of DBA:naphthalene (IS) in oil. Data are presented as mean+se, n=3.
Figure 7:
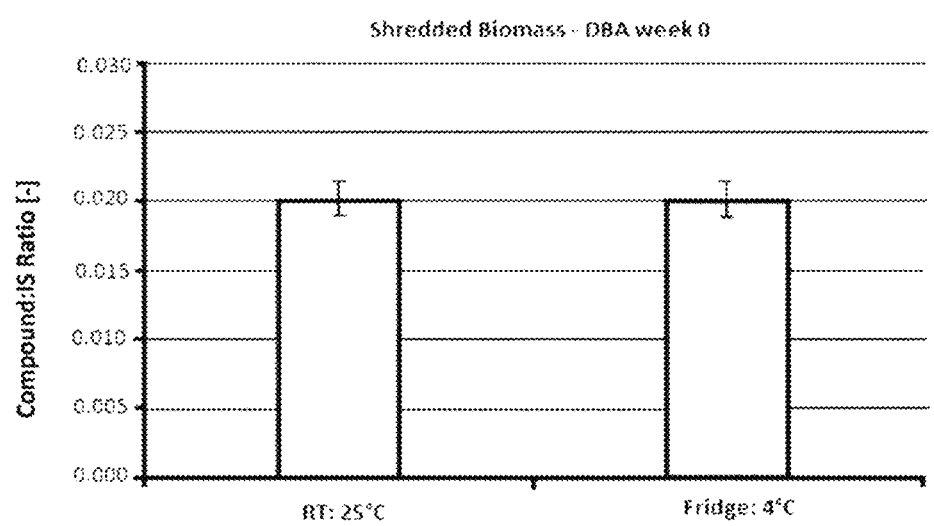
FIG. 7 shows the amount of a bioactive, DBA, in compositions prepared by extracting homogenised biomass of *Asparagopsis* into oil for a period of 10 days followed by immediate storage (week 0) at the shown temperatures (25° C./"RT" or 4° C./"Fridge"). Shown is the ratio of DBA: naphthalene (IS) in oil. Data are presented as mean+se, n=3.

FIGS. 6 and 7 demonstrate the extraction of DBA, a bioactive agent, from biomass of *Asparagopsis* into an oil, to form an *Asparagopsis* oil composition.

Given the above results it can be seen that the clarified oil compositions (i.e. with *Asparagopsis* biomass removed) had a stable shelf-life of at least one year (65 weeks) at 4° C., and at least 12 weeks at room temperature (25° C.). In contrast, water extracts remained stable for 8 weeks and deteriorated thereafter, regardless of the storage temperature. This result is surprising, as it is expected that storage at lower temperatures, regardless of the storage medium (water- or oil-based), should provide a longer shelf life.

Example 3: Maximising Biomass Extraction into Oil

The extraction method from Example 1 which provided the highest concentration of bioactive (bromoform) detected in oil in the shortest amount of time (e.g. homogenisation and extraction into oil) was used to quantify the maximum amount of *Asparagopsis* biomass that can be extracted.

Figure 12:
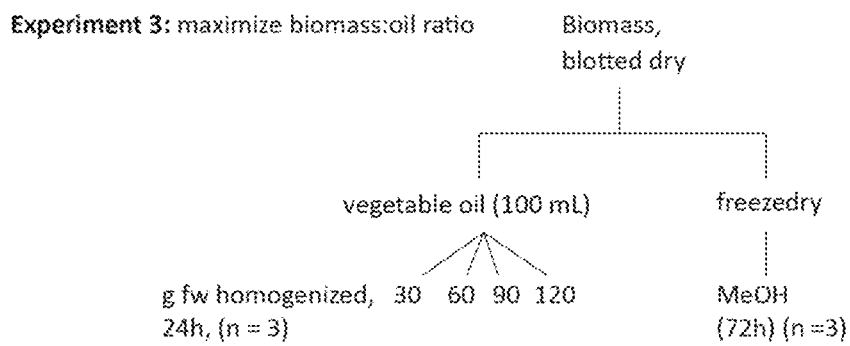
FIG. 12 shows the experimental design for quantification of the maximum amount of *Asparagopsis* biomass that can be extracted, as described in Example 3.

*Asparagopsis taxiformis* (gametophyte stage) was collected from Magnetic Island (QLD, Australia). Fresh biomass was blotted dry and samples of the following mass were collected into separate 250 mL glass bottles prefilled with 100 mL vegetable oil: 30.0 g, 60.0 g, 90.0 g, and 120.0 g fw (n=3 for each amount). All bottles were securely capped and stored on ice for immediate transport to the laboratory for further processing and analysis. Replicate samples (n=3) of blotted biomass (30.0 g fw) were also collected for determination of dry weight, as shown in the Experimental Design of FIG. 12.

In the laboratory, biomass was homogenised (IKA ultra-turrax T-25) in oil, and the samples were stored at 4° C. for 24 h before quantification of bromoform, as described above.

FIGS. 8 and 9 show the amount of bioactive (bromoform) extracted from different amounts of *Asparagopsis* biomass (in an identical volume of oil). FIG. 8 shows increasing the *Asparagopsis* biomass: oil ratio resulted in a corresponding increase in the amount of bioactive extracted into the oil. This data demonstrates the level of a bioactive agent, bromoform, from biomass of *Asparagopsis* into an oil, is increased by increasing the ratio of biomass to oil.

At higher ratios of biomass: oil, a solid, opaque gel formed and it was not possible to fully homogenise the biomass into the oil. For example, a solid, opaque gel was formed when 90 g or 120 g of homogenised biomass was homogenised into 100 mL of oil. This gelling also made it very laborious to separate out 1 mL of clarified oil, which was required for partitioning with methanol for GC/MS-analysis.

Subsamples from the 120 g-treatment comprising the gel were heated (1 h, 60° C., water bath) prior to centrifugation. This resulted in a 20% higher yield of bioactive in the oil compared with centrifugation of non-heated samples (see FIGS. 8 and 9). *Asparagopsis* contains sulfated cell wall polysaccharides which are typically water soluble. Without wishing to be bound by theory, it is postulated that a gel/emulsion formed between extracted polysaccharides, the oil, and residual external and internal water on and in the biomass. With higher amounts of polysaccharides being extracted at higher ratios of biomass: oil, this resulted in the formation of the gel. It is clear the gel comprises bioactive agents (such as bromoform); upon heating the gel releases bromoform, which is then transferred to the oil of the *Asparagopsis* oil composition.

Example 4: Examination of *Asparagopsis* Oil Composition Reduction of Methane Production In Vivo Fistulated steers (*Bos indicus*) are used for an in vivo feeding trial. All the animals are fistulated and trained in respiration chambers prior to the commencement of the experimental period. Initially steers are held on Flinders grass hay, in group pens (cattle yards) for four days. Subsequently, steers are divided into two groups and allocated to treatments group, control (Flinders grass hay only) and *Asparagopsis* oil composition supplementation. Selection of the dose of *Asparagopsis* oil composition is based on results obtained from a previous in vitro study investigating methane reduction potential.

The fresh weight to dry weight ratio of blotted dry *Asparagopsis* is 10 (i.e. 30 g fw=3 g dw). Assuming a content of organic matter (OM) of 80% of dw (Machado et al., 2014), the corresponding content of OM originating from *Asparagopsis* in the tested biomass/oil mixtures range from 0.024-0.096 g OM·mL$^{-1}$ (Table 1):

TABLE 1

The content of organic matter originating from *Asparagopsis* biomass in biomass/oil mixtures at increasing ratios, and the volume** required for a dose in feed equivalent of 0.1-3% OM *Asparagopsis*.

| Amount (g) of *Asparagopsis* in oil | | | | Volume oil (mL) required to achieve equivalent dose of 0.1-3.0% *Asparagopsis* OM in 100 g feed** | | |
|---|---|---|---|---|---|---|
| fw/100 mL | fw/ mL | dw/ mL | *Asparagopsis* OM/mL | 0.1 Asp OM eq. | 1.0 Asp OM eq. | 3.0 Asp OM eq. |
| 30 | 0.3 | 9.03 | 0.024 | 4.17 | 41.7 | 125.0 |
| 60 | 0.6 | 0.06 | 0.048 | 2.08 | 20.8 | 62.5 |
| 90 | 0.9 | 0.09 | 0.072 | 1.39 | 13.9 | 41.7 |
| 120 | 1.2 | 0.12 | 0.096 | 1.04 | 10.4 | 31.3 |
| 150 | 1.5 | 0.15 | 0.12 | 0.83 | 8.3 | 25.0 |

**This volume is based on the oil being separated from the biomass. For example, adding 120 g fw seaweed to 100 mL oil increases the final volume of the mixture. Being 90% water (fw:dw ratio of 10), and for the ease of calculation, assuming the density of *Asparagopsis* to be equal to water, and therefore the volume of the biomass:oil mixture to increase accordingly with the amount of biomass added (i.e. 100 mL oil + 150 g fw *Asparagopsis* = 250 mL mixture, corresponding to 15 g dw *Asparagopsis* = 12 g OM *Asparagopsis*/250 mL = 0.048 g *Asparagopsis* OM/mL homogenous mixture).

Based on the data discussed above, beyond a ratio of biomass:oil is 150 g fw: 100 mL a homogenous mixture may not be formed. A dose of 1% OM *Asparagopsis* is practical at a biomass: oil ratio ≥120 g/100 mL. It has been demonstrated that a dose of 0.2% OM *Asparagopsis* is effective to inhibit methanogensis in animals in vivo, therefore, a volume of only 2.08 mL oil (or 4.6 mL of biomass/oil mixture) needs to be added to 100 g feed for the 120 g fw biomass/100 mL oil mixture.

To calculate the volume of oil required to achieve a dose equivalent to a desired % level of the organic matter administered to the ruminant animal, the % organic matter amount of the *Asparagopsis* oil compositions described herein is calculated from the fresh weight (fw) of *Asparagopsis* biomass contacted with a defined volume of at least one oil. The fresh weight to dry weight (dw) ratio of blotted dry *Asparagopsis* is 10 (i.e. 30 g fw=3 g dw). Assuming a content of organic matter (OM) of 80% of dw based on previous data, the corresponding content of OM originating from *Asparagopsis* in the biomass/oil can be calculated. For example, for an *Asparagopsis* oil composition comprising 30 g fresh weight (fw) *Asparagopsis* biomass in 100 mL of at least one oil is equivalent to 0.024 *Asparagopsis* organic matter/mL. If the desired level of inclusion in fees is 0.1% *Asparagopsis* OM in 100 g feed, then 4.17 mL of the 30 g fw/100 mL *Asparagopsis* oil composition is required per 100 g of feed.

The steers are allocated into individual pens in the research station with ad libitum Flinders grass hay and water supply. Animals under *Asparagopsis* oil composition supplement are dosed directly into the rumen before morning feed to ensure complete intake of the *Asparagopsis* oil composition and consistency of treatment intake between animals, or *Asparagopsis* oil composition is added to feed as described above. An acclimation period of 14 days to the different diets is provided before going into open-circuit respiration chambers for measurement of methane production over 48 h. Methane production of animals is measured after 7, 14, 21 and/or 29 days of treatment to evaluate the efficacy of *Asparagopsis* oil compositions in reducing methane production in animals over time. After 31 days the Asparagopsis oil composition is ceased and the animals are reallocated to paddocks. Rumen samples are collected 4 h after Asparagopsis oil composition was inserted intra-ruminally or after feeding (e.g. at day 1, 15, 22, and 30 of Asparagopsis oil composition treatment) to evaluate changes in VFA production and acetate to propionate ratios. Live weight, and feed offered and refused are measured daily and total dry matter (DM) intake and total organic matter (OM) intake calculated to determine mean individual DM and OM intakes. At all time-points tested, mean methane production is calculated.

Example 5: Examination of Asparagopsis Oil Composition Reduction of Methane Production In Vivo in Sheep Methodology Merino cross wethers are allocated to one of five groups based on the daily inclusion rate (organic matter, OM basis) of Asparagopsis oil composition [0 (control), 0.1, 0.5, 1.0, 2.0, 3.0%]. Inclusion rates (% OM intake) are calculated as shown using the calculations shown in Table 1 and Example 4.

Sheep are maintained under animal house conditions and fed a pelleted commercial shipper ration based on lupins, oats, barley, wheat with cereal straw as the roughage component [chemical composition (g/kg DM) of ash, 72; crude protein (CP) 112; neutral detergent fibre (aNDFom) 519; acid detergent fibre (ADFom) 338, and free of cobalt, selenium and rumen modifiers] at 1.2× maintenance throughout the study. All sheep are dosed with a Co bullet prior to the commencement of the experimental period.

Sheep are gradually adapted to Asparagopsis oil composition over an initial two weeks by mixing the ground material with 200 g crushed lupins (lupin diet). The Asparagopsis oil composition/lupin mix is then added to the pelleted ration, mixed and fed for a further 75 d.

Feed intake is recorded daily and liveweight (LW) measured at 14 d intervals throughout the trial.

Three measurements of individual animal methane production (g/kg DM intake) are conducted, the first after 30 d Asparagopsis oil composition inclusion and then at 21 d intervals throughout the trial period. During 24 h methane measurements using open circuit respiration chambers as described by Li (2013) [PhD thesis; Eremophila glabra reduced methane production in sheep, University of Western Australia] feed on offer (pellets/lupins) is proportionally reduced to 1.0× maintenance to ensure consistent intakes.

Following each methane measurement, up to 50 mL rumen fluid is collected by stomach tube for the determination of volatile fatty acid (VFA) concentration.

Statistical Analysis

The statistical analysis is conducted by fitting linear mixed models to each response variable. These models are able to account for the design of the experiment (the allocation of animals to particular groups and chambers), the structure of the data (repeated measures) and any missing values which occur. The "fixed effects" in the mixed model consisted of the treatment effect (different inclusion rates of Asparagopsis taxiformis), the time effect (sampling dates), the treatment by time interaction, and any covariates. Initial live weight is included as a covariate when analysing live weight. It is also tested as a potential covariate for other response variables.

Means for all combinations of treatment and time, adjusted for all other terms in the model are calculated. P-values are calculated for testing the overall effect of time, treatment, and their interaction. Least significant differences (P=0.05) are calculated for comparing pairs of means.

The following are measured:
Intakes of feed comprising Asparagopsis oil compositions
Dry matter degraded in vivo
animal liveweight
total VFA concentration
molar proportions of individual VFA I (including acetate, propionate), excluding iso-butyrate
methane emissions (g/kg DM intake)

The invention claimed is:

1. A process for preparing an Asparagopsis oil composition, said process comprising the steps of:
   (a) providing a biomass of Asparagopsis;
   (b) providing at least one oil; and
   (c) contacting the biomass with the at least one oil under conditions to extract at least one bioactive agent from the biomass into the at least one oil to form the Asparagopsis oil composition.

2. The process according to claim 1, wherein step (c) includes homogenising the biomass in the at least one oil.

3. The process according to claim 1, further comprising, following step (c), a step of separating said biomass from said at least one oil.

4. The process according to claim 1, wherein the ratio of biomass to the at least one oil is greater than 0.3 g: 1 mL, greater than 0.6 g: 1 mL, greater than 0.9 g: 1 mL or greater than 1.2 g: 1 mL.

5. The process according to claim 1, wherein step (c) is performed for a period of at least 1, 2, 3, 4, 5, 6, 7, 8, 9, or 10 days.

6. The process according to claim 1, wherein step (c) is performed at a temperature of about 4° C.

7. The process according to claim 3, wherein prior to the step of separating said biomass from said at least one oil, the biomass contacted with the at least one oil is heated, such that a gel comprising the at least one bioactive agent releases said at least one bioactive agent to the at least one oil.

8. The process according to claim 7, wherein the biomass contacted with the at least one oil is heated to a temperature of 60° C.

9. The process according to claim 7, wherein the biomass contacted with the at least one oil is heated for a period of one hour.

10. The process according to claim 1, wherein said Asparagopsis is Asparagopsis taxiformis and/or Asparagopsis armata.

11. The process according to claim 1, wherein the step of providing a biomass of Asparagopsis does not include air drying of the biomass.

12. The process according to claim 1, wherein the step of providing a biomass of Asparagopsis comprises collecting the biomass into the at least one oil.

13. The process according to claim 1, wherein the at least one oil comprises an edible oil.

14. The process according to claim 1, wherein the at least one bioactive agent is selected from the group consisting of bromochloroacetic acid (BCA), bromoform (BF), dibromoacetic acid (DBA), and dibromochloromethane (DBCM).

* * * * *